(12) United States Patent
Shi et al.

(10) Patent No.: US 10,022,720 B2
(45) Date of Patent: Jul. 17, 2018

(54) FLUIDIC UNITS AND CARTRIDGES FOR MULTI-ANALYTE ANALYSIS

(71) Applicant: CYTOCHIP INC., Duarte, CA (US)

(72) Inventors: Wendian Shi, Monrovia, CA (US); Yuzhe Ding, Monrovia, CA (US)

(73) Assignee: CYTOCHIP INC., Irvine, CA (US)

( * ) Notice: Subject to any disclaimer, the term of this patent is extended or adjusted under 35 U.S.C. 154(b) by 59 days.

(21) Appl. No.: 15/176,729

(22) Filed: Jun. 8, 2016

(65) Prior Publication Data

US 2016/0361715 A1     Dec. 15, 2016

Related U.S. Application Data

(60) Provisional application No. 62/174,776, filed on Jun. 12, 2015.

(51) Int. Cl.
*A61J 1/06*     (2006.01)
*B01L 3/00*     (2006.01)
(Continued)

(52) U.S. Cl.
CPC .... *B01L 3/50273* (2013.01); *A61B 5/150022* (2013.01); *A61B 10/0096* (2013.01); *B01L 3/502715* (2013.01); *B01L 3/502723* (2013.01); *B01L 3/502738* (2013.01); *B01L 2200/141* (2013.01); *B01L 2200/143* (2013.01); *B01L 2300/0627* (2013.01); *B01L 2300/0645* (2013.01); *B01L 2300/0681* (2013.01); *B01L 2300/087* (2013.01); *B01L 2300/0861* (2013.01); *B01L 2300/0864* (2013.01);
(Continued)

(58) Field of Classification Search
CPC ............... A61J 1/06; B01L 3/00; G01N 21/00
USPC .............. 422/68.1, 502, 503, 554, 560, 561; 436/43, 180
See application file for complete search history.

(56) References Cited

U.S. PATENT DOCUMENTS

| | | | |
|---|---|---|---|
| 4,895,500 A | 1/1990 | Hok et al. | |
| 4,983,523 A | 1/1991 | Li et al. | |

(Continued)

FOREIGN PATENT DOCUMENTS

| | | |
|---|---|---|
| WO | 2016/200922 A1 | 12/2016 |
| WO | 2017/011554 A1 | 1/2017 |

OTHER PUBLICATIONS

Al-Faqheri et al., Development of a passive liquid valve (PLV) utilizing a pressure equilibrium phenomenon on the centrifugal microfluidic platform. Sensors, 15(3):4658-4676 (2015).
(Continued)

*Primary Examiner* — Brian J. Sines
(74) *Attorney, Agent, or Firm* — K&L Gates LLP; Louis C. Cullman; Joseph F. Arand

(57) ABSTRACT

A fluidic device for a cartridge for testing biological samples is disclosed herein. In an embodiment, the fluidic device includes a fluidic chamber, at least one microfluidic channel in fluid communication with the fluidic chamber, a venting port configured to apply a pneumatic force to the fluidic chamber, at least one passive valve located within the at least one microfluidic channel and configured to allow or stop fluid flow through the at least one microfluidic channel based on a pressure difference, and a controller configured to control the pneumatic force applied to the fluidic chamber via the venting port.

30 Claims, 17 Drawing Sheets

(51) Int. Cl.
  *G01N 21/00* (2006.01)
  *A61B 5/15* (2006.01)
  *A61B 10/00* (2006.01)

(52) U.S. Cl.
  CPC .......... *B01L 2300/0867* (2013.01); *B01L 2300/0887* (2013.01); *B01L 2300/14* (2013.01); *B01L 2400/0406* (2013.01); *B01L 2400/0409* (2013.01); *B01L 2400/0457* (2013.01); *B01L 2400/0487* (2013.01); *B01L 2400/0688* (2013.01); *B01L 2400/088* (2013.01)

(56) References Cited

U.S. PATENT DOCUMENTS

| | | | |
|---|---|---|---|
| 5,096,669 A | 3/1992 | Lauks et al. | |
| 5,110,724 A | 5/1992 | Hewett | |
| 5,213,965 A | 5/1993 | Jones | |
| 5,409,665 A | 4/1995 | Burd | |
| 5,478,750 A | 12/1995 | Bernstein et al. | |
| 5,591,643 A | 1/1997 | Schembri | |
| 6,100,084 A | 8/2000 | Miles et al. | |
| 6,369,893 B1 | 4/2002 | Christel et al. | |
| 6,382,228 B1 | 5/2002 | Cabuz et al. | |
| 6,549,275 B1 | 4/2003 | Cabuz et al. | |
| 6,664,110 B1 | 12/2003 | Tsuji et al. | |
| 6,750,060 B2 | 6/2004 | Ozasa et al. | |
| 6,752,961 B2 | 6/2004 | Kopf-Sill et al. | |
| 6,804,984 B2 | 10/2004 | Shibata | |
| 7,016,022 B2 | 3/2006 | Fritz et al. | |
| 7,061,595 B2 | 6/2006 | Cabuz et al. | |
| 7,113,266 B1 | 9/2006 | Wells | |
| 7,130,046 B2 | 10/2006 | Fritz et al. | |
| 7,172,897 B2 | 2/2007 | Blackburn et al. | |
| 7,215,425 B2 | 5/2007 | Rezachek et al. | |
| 7,220,595 B2 | 5/2007 | Nugent et al. | |
| 7,328,722 B2 | 2/2008 | Rich et al. | |
| 7,420,659 B1 | 9/2008 | Cabuz et al. | |
| 7,471,394 B2 | 12/2008 | Padmanabhan et al. | |
| 7,521,243 B2 | 4/2009 | Lindberg et al. | |
| 7,534,331 B2 | 5/2009 | Kayyem | |
| 7,553,453 B2 | 6/2009 | Gu et al. | |
| 7,580,120 B2 | 8/2009 | Hamada et al. | |
| 7,595,169 B2 | 9/2009 | Swaim et al. | |
| 7,632,462 B2 | 12/2009 | Holtlund et al. | |
| 7,641,856 B2 | 1/2010 | Padmanabhan et al. | |
| 7,760,351 B2 | 7/2010 | Cox et al. | |
| 7,771,658 B2 | 8/2010 | Larsen | |
| 7,800,742 B2 | 9/2010 | Fukuda et al. | |
| 7,832,429 B2 | 11/2010 | Young et al. | |
| 7,842,234 B2 | 11/2010 | Lauks et al. | |
| 7,843,563 B2 | 11/2010 | Fritz et al. | |
| 7,863,035 B2 | 1/2011 | Clemens et al. | |
| 7,894,047 B2 | 2/2011 | Hamada et al. | |
| 7,910,062 B2 | 3/2011 | Yu et al. | |
| 8,029,746 B2 | 10/2011 | Yu et al. | |
| 8,034,296 B2 | 10/2011 | Cox et al. | |
| 8,071,051 B2 | 12/2011 | Padmanabhan et al. | |
| 8,097,225 B2 | 1/2012 | Padmanabhan et al. | |
| 8,124,024 B2 | 2/2012 | Ching et al. | |
| 8,168,443 B2 | 5/2012 | Yu et al. | |
| 8,202,492 B2 | 6/2012 | Linder et al. | |
| 8,283,177 B2 | 10/2012 | Ball et al. | |
| 8,293,175 B2 | 10/2012 | Holtlund et al. | |
| 8,367,023 B2 | 2/2013 | Bae et al. | |
| 8,383,043 B2 | 2/2013 | Padmanabhan et al. | |
| 8,518,328 B2 | 8/2013 | Padmanabhan et al. | |
| 8,540,946 B2 | 9/2013 | Padmanabhan et al. | |
| 8,545,756 B2 | 10/2013 | Holtlund et al. | |
| 8,567,425 B2 | 10/2013 | Tan et al. | |
| 8,573,033 B2 | 11/2013 | Larsen | |
| 8,591,829 B2 | 11/2013 | Taylor et al. | |
| 8,646,842 B2 | 2/2014 | Barfuss | |
| 8,663,583 B2 | 3/2014 | Kelley et al. | |
| 8,741,233 B2 | 6/2014 | Bardell et al. | |
| 8,741,234 B2 | 6/2014 | Wang et al. | |
| 8,741,235 B2 | 6/2014 | Janisch et al. | |
| 8,828,320 B2 | 9/2014 | Bardell et al. | |
| 8,846,380 B2 | 9/2014 | Bae et al. | |
| 8,980,635 B2 | 3/2015 | Kelley et al. | |
| 9,029,158 B2 | 5/2015 | Tai et al. | |
| 9,140,694 B2 | 9/2015 | Holtlund et al. | |
| 9,234,884 B2 | 1/2016 | Tai et al. | |
| 9,494,570 B2 | 11/2016 | Bransky et al. | |
| 2002/0042125 A1 | 4/2002 | Petersen et al. | |
| 2004/0005247 A1 | 1/2004 | Karp | |
| 2005/0136552 A1 | 6/2005 | Buechler | |
| 2007/0039835 A1 | 2/2007 | Rossier et al. | |
| 2007/0154351 A1 | 7/2007 | Bae et al. | |
| 2008/0199971 A1 | 8/2008 | Tondra | |
| 2009/0075390 A1 | 3/2009 | Linder et al. | |
| 2009/0291507 A1 | 11/2009 | Clemens et al. | |
| 2010/0288689 A1 | 11/2010 | Zhu et al. | |
| 2013/0130262 A1 | 5/2013 | Battrell et al. | |
| 2013/0343955 A1 | 12/2013 | Doyle et al. | |
| 2013/0344475 A1 | 12/2013 | Jovanovich et al. | |
| 2014/0038809 A1 | 2/2014 | Bransky et al. | |
| 2014/0301915 A1 | 10/2014 | Doyle et al. | |
| 2014/0349381 A1 | 11/2014 | Battrell et al. | |
| 2015/0151295 A1* | 6/2015 | Kimura | B01L 3/50273 435/289.1 |
| 2016/0129445 A1* | 5/2016 | Corey | B01L 7/52 435/286.1 |
| 2016/0130640 A1* | 5/2016 | Wright | B01F 7/00116 506/39 |
| 2017/0016753 A1 | 1/2017 | Shi et al. | |

OTHER PUBLICATIONS

Ducree et al., The centrifugal microfluidic Bio-disk platform. Journal of Micromechanics and Microengineering, vol. 17:S103-S115 (2007).

Henning, Micro-Pneumatic Logic. 2004 ASME International Mechanical Engineering Congress and RD&D Expo, Anaheim, CA, Nov. 15-21, 2004.

International Search Report and Written Opinion issued in International Application No. PCT/US2016/036426 dated Sep. 6, 2016, 13 pages.

International Search Report and Written Opinion issued in International Application No. PCT/US2016/042089 dated Dec. 8, 2016, 14 pages.

* cited by examiner

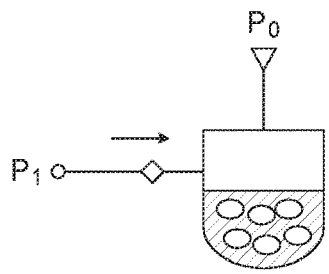
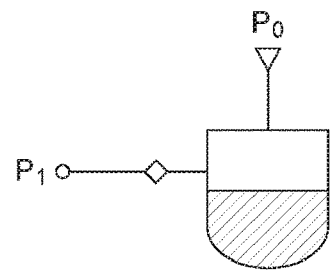
FIG. 6A  FIG. 6B
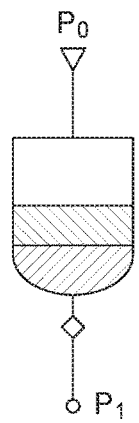
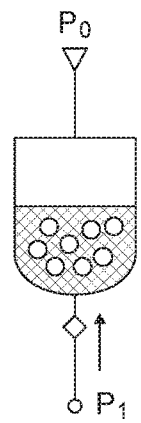
FIG. 7A  FIG. 7B
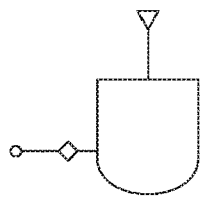
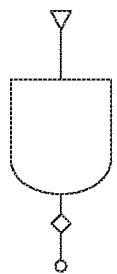
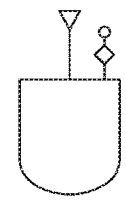
FIG. 8A  FIG. 8B  FIG. 8C
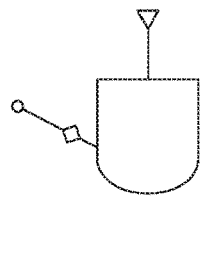
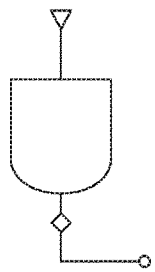
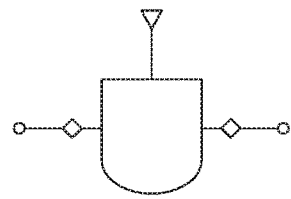
FIG. 8D  FIG. 8E  FIG. 8F

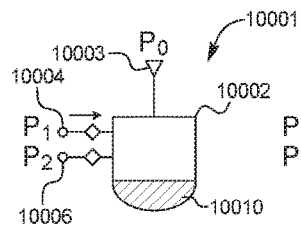
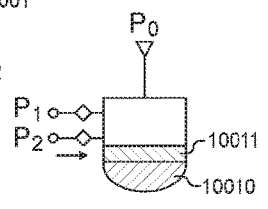
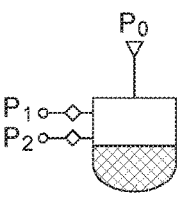
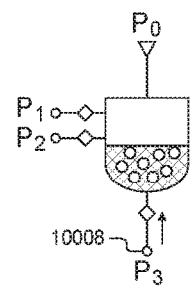
FIG. 10A    FIG. 10B    FIG. 10C    FIG. 10D
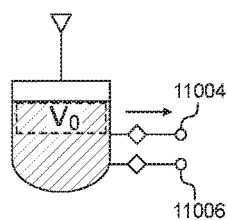
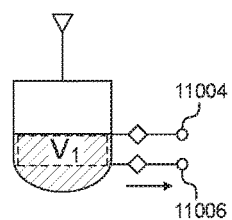
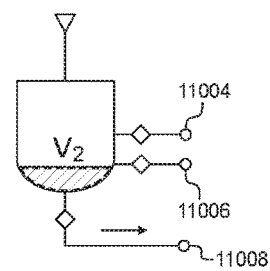
FIG. 11A    FIG. 11B    FIG. 11C
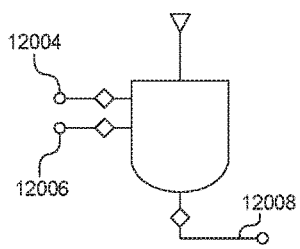
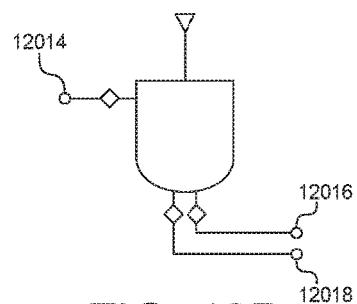
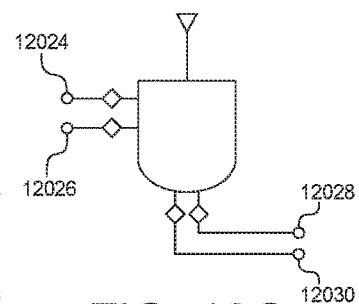
FIG. 12A    FIG. 12B    FIG. 12C
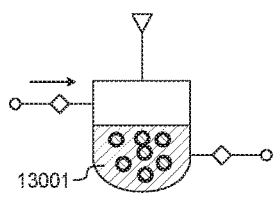
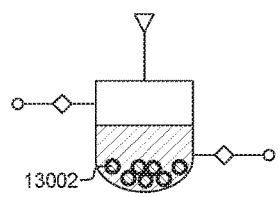
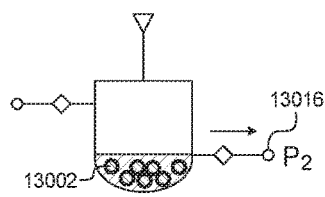
FIG. 13A    FIG. 13B    FIG. 13C

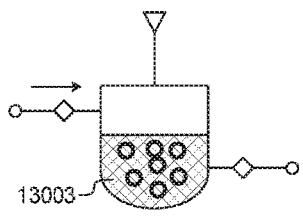
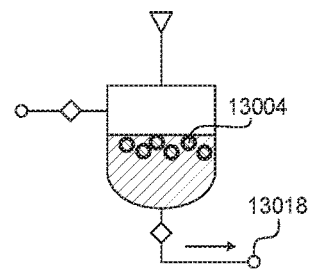
FIG. 13D  FIG. 13E
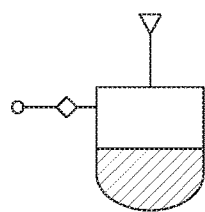 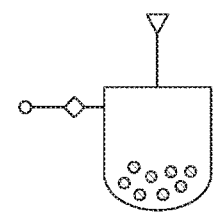 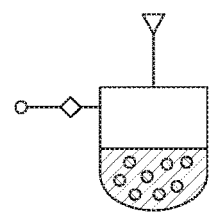
FIG. 14A  FIG. 14B  FIG. 14C
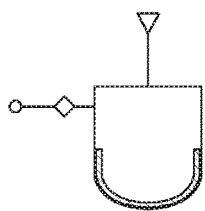 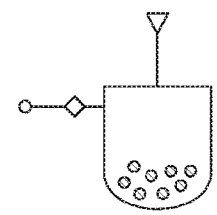 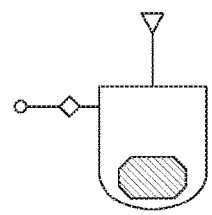
FIG. 14D  FIG. 14E  FIG. 14F
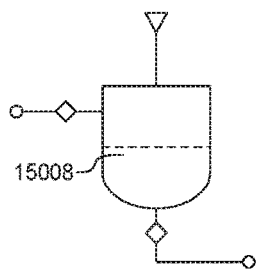 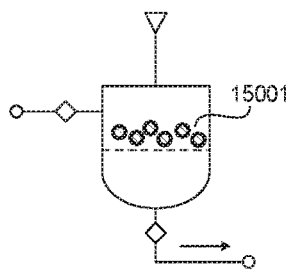 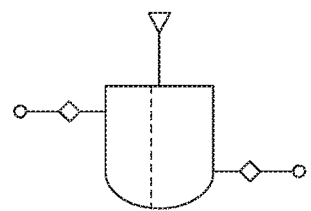
FIG. 15A  FIG. 15B  FIG. 15C
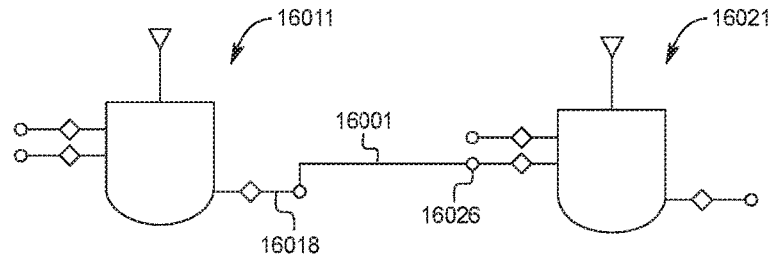
FIG. 16

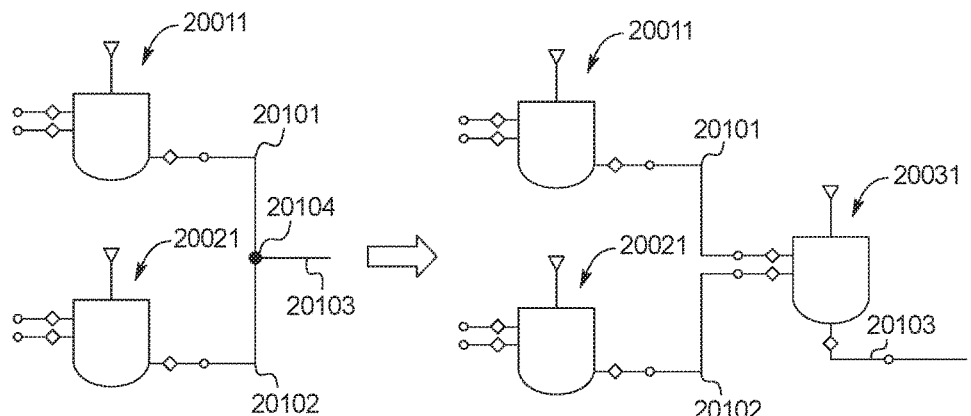
FIG. 20A
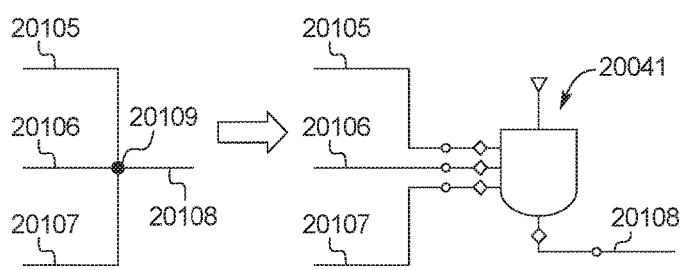 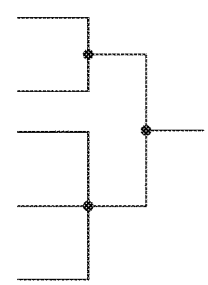
FIG. 20B  FIG. 20C
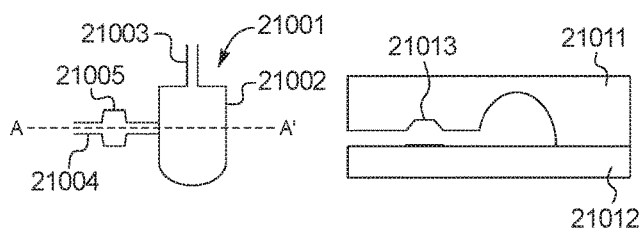 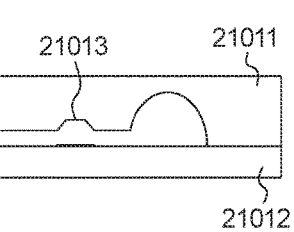 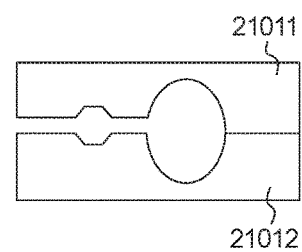
FIG. 21A  FIG. 21B  FIG. 21C
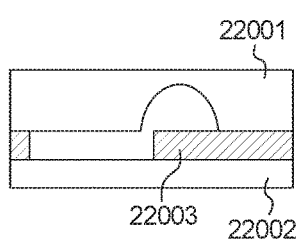 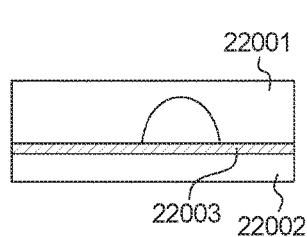 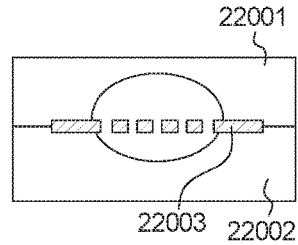
FIG. 22A  FIG. 22B  FIG. 22C

FLUIDIC UNITS AND CARTRIDGES FOR MULTI-ANALYTE ANALYSIS

PRIORITY CLAIM

This application claims priority to U.S. Provisional Patent Application No. 62/174,776, entitled "Fluidic Units and Cartridges for Multi-Analyte Analysis", filed Jun. 12, 2015, the entire contents of which are hereby incorporated by reference and relied upon.

FIELD OF THE DISCLOSURE

The present disclosure relates generally to methods and apparatuses for multi-analyte analyses, and more specifically to fluidic units and cartridges for multi-analyte analyses.

BACKGROUND OF THE DISCLOSURE

In the field of in-vitro diagnostics, analyses are often made on biological samples, such as body fluids (e.g. blood, urine, saliva, cerebrospinal fluid, etc.), cell suspension (e.g. tissue cells suspension in buffer), and other fluid samples. For certain scenarios, such as point-of-care testing, it is desirable to perform the above analysis in the format of a cartridge device. It is also desirable that the cartridge is disposable after each use to avoid cross-contamination. Microfluidic technologies can be used to build these cartridge devices, due to the merits of a small sample volume and a small cartridge size. However, cartridge devices that can be used to measure multiple biological markers are still lacking.

SUMMARY OF THE DISCLOSURE

In one aspect, the present disclosure is directed to a design of a fluidic unit to construct cartridges for testing biological samples. The fluidic unit comprises a chamber, a venting port and at least one microfluidic channel that accesses the chamber and has a passive valve. The operation of this unit depends on gravity or another force as a replacement for gravity, such as a centrifugal force, to keep fluid in position. In addition, it uses another force such as pneumatic pressure to transfer fluid. The design of this fluidic unit has an intrinsic "self-stop" mechanism, which is configured to overcome the challenge of accurate volume transfer in pneumatically actuated cartridges. This fluidic unit can be modified to achieve various fluidic functions, such as mixing samples, removing bubbles, transferring a fixed-volume, relaying fluid flow, etc. With a plurality of these fluidic units, more sophisticated fluidic functions can be achieved, such as serial dilution, replacing T-junctions in microfluidic, etc. The fluidic unit can also be implemented by a structure including a plurality of layers. In an embodiment, the fluidic unit can be implemented as a two-layer structure. In another embodiment, the fluidic unit can be implemented as a three-layer structure.

The present disclosure also explains how to design cartridges with the fluidic unit to test various biological samples. The cartridges can have a plurality of design units and optionally other fluidic components such as fluidic conduits, valves and pumps, etc. The cartridge devices can be used for tests such as Complete Blood Count, Flow Cytometer Analysis, Blood Chemistry, Blood Gas, Immunoassay, Nucleic Acid purification, and Molecular Diagnostics, etc. The present disclosure is optimal for integrating multiple of the above tests into one cartridge.

For embodiments of cartridges that depend on gravity, it is desirable to maintain a vertical position. In these cartridges, the accuracy of transferring a fixed volume of fluid is sensitive to tilting away from the vertical position. The present disclosure introduces methodologies to reduce or eliminate the effect of tilting.

The cartridges are inserted into a reader to read out measurement signals. The present disclosure is also directed to multiple reader designs to work with cartridges of the fluidic unit. One reader device accepts only one cartridge at a time. Another reader device can simultaneously accept multiple cartridges, wherein the cartridges are run in serial, in parallel or in streamline to increase test throughput.

In a general example embodiment, a fluidic device includes a fluidic chamber, at least one microfluidic channel in fluid communication with the fluidic chamber, a venting port configured to apply a pneumatic force to the fluidic chamber, at least one passive valve located within the at least one microfluidic channel and configured to allow or stop fluid flow through the at least one microfluidic channel based on a pressure difference, and a controller configured to control the pneumatic force applied to the fluidic chamber via the venting port.

In another embodiment, the fluidic chamber is located within a disposable cartridge configured to be held in a vertical position by a housing of the fluidic device.

In another embodiment, the venting port is located at a top portion of the fluidic chamber when the fluidic chamber is held in the vertical position.

In another embodiment, the at least one microfluidic channel is located a height below the venting port when the fluidic chamber is held in the vertical position.

In another embodiment, the at least one microfluidic channel includes a first microfluidic channel and a second microfluidic channel, the first microfluidic channel located a height above the second microfluidic channel with the fluidic chamber is held in the vertical position.

In another embodiment, the at least one passive valve includes at least one of: (i) a hydrophobic patch; (ii) a hydrophilic patch; (iii) a sudden diameter enlargement of a hydrophobic channel; and (iv) a sudden diameter shrink of a hydrophobic channel.

In another embodiment, the controller is configured to control the pneumatic force applied to the fluidic chamber via the venting port based on (i) a pressure ($P_0$) associated with the venting port, and (ii) a pressure ($P_1$) associated with the at least one microfluidic channel. The pressure difference ($P_0-P_1$) provides the pneumatic force to drive fluid and air.

In another embodiment, the controller is configured to store fluid in the fluidic chamber by controlling the pneumatic force applied to the fluidic chamber via the venting port according to the following equations: $-\Delta P_{in}-\rho gh \leq P_0-P_1 \leq \Delta P_{out}-\rho gh$, if $h \geq 0$; and $P_1-P_0 \leq \Delta P_{in}$, if $h<0$, wherein (i) $\Delta P_{in}$ is a first threshold pressure associated with a first direction of fluid entering the fluidic chamber, (ii) $\Delta P_{out}$ is a second threshold pressure associated with a second direction of fluid leaving the fluidic chamber, and (iii) $\rho gh$ is the hydraulic pressure of the fluid that is caused by the gravity or a replacement for gravity such as centrifugal force.

In another embodiment, the controller is configured to transfer fluid into the fluidic chamber by controlling the pneumatic force applied to the fluidic chamber via the venting port according to the following equations: $P_1-P_0>\Delta P_{in}+\rho gh$, if $h \geq 0$; and $P_1-P_0>\Delta P_{in}$, if $h<0$, wherein (i) $\Delta P_{in}$ is a threshold pressure associated with a direction of fluid entering the fluidic chamber, and (ii) ρgh is the hydraulic pressure of the fluid.

In another embodiment, the controller is configured to transfer fluid out of the fluidic chamber by controlling the pneumatic force applied to the fluidic chamber via the venting port according to the following equation: $P_0-P_1>\Delta P_{out}-\rho gh$, wherein (i) $\Delta P_{out}$ is a threshold pressure associated with a direction of fluid leaving the fluidic chamber, and (ii) ρgh is the hydraulic pressure of the fluid.

In another embodiment, the fluidic chamber includes a filter membrane with a pore size smaller than known particles in the fluid.

In another embodiment, the device includes a plurality of fluidic chambers, and wherein the controller controls the pneumatic pressure applied to respective venting ports of the plurality of fluidic chambers independently of each other.

In another embodiment, the plurality of fluidic chambers includes a first fluidic chamber and a second fluidic chamber, the first fluidic chamber and the second fluidic chamber in fluid communication via only one microchannel.

In another general example embodiment, a fluid testing system includes a device including a pneumatic source and a controller configured to control the pneumatic source, and a fluidic cartridge configured to be inserted into the device, the fluidic cartridge including an inlet port configured to receive a fluid sample, a sample retaining chamber configured to receive the fluid sample from the inlet port, a first fluidic chamber configure to store or receive a reagent, the first fluidic chamber in fluid communication with the sample retaining chamber, and a second fluidic structure in fluid communication with the sample retaining chamber.

In another embodiment, the controller is configured to mix the fluid sample with the reagent in the second fluidic structure by activating the pneumatic source to cause the reagent from the first fluidic chamber to flush the fluid sample into second fluidic structure.

In another embodiment, the second fluidic structure includes a sensing structure, and wherein the controller is configured to push the fluid sample first and the reagent second through the sensing structure.

In another embodiment, the second fluidic chamber includes a filter membrane with a pore size smaller than target cells in the fluid sample.

In another embodiment, the sample retaining chamber is positioned and arranged to draw the fluid sample through the inlet port by capillary force.

In another general example embodiment, a fluidic device includes a fluidic chamber, at least one microfluidic channel in fluid communication with the fluidic chamber, a tilt sensor configured to sense a tilt angle of the fluidic chamber, and a controller configured to determine a volume of fluid to be pumped into or out of the fluidic chamber via the at least one microfluidic channel based on the tilt angle sensed by the tilt sensor.

In another embodiment, the device includes a venting port configured to apply a pneumatic force to the fluidic chamber, and wherein the controller is configured to control the pneumatic force applied to the fluidic chamber via the venting port to expel the volume of fluid from the fluidic chamber.

In another embodiment, the controller is configured to determine the volume of fluid based on a shape of the fluidic chamber and the tilt angle sensed by the tilt sensor.

BRIEF DESCRIPTION OF THE DRAWINGS

Embodiments of the present disclosure will now be explained in further detail by way of example only with reference to the accompanying figures, in which:

FIGS. 6A and 6B show an example embodiment of fluid transfer with an example embodiment of a fluidic unit according to the present disclosure;

FIGS. 7A and 7B show an example embodiment of fluid transfer with an example embodiment of a fluidic unit according to the present disclosure;

FIGS. 8A to 8J shows the designs of example embodiments of fluidic units according to the present disclosure;

FIGS. 10A to 10D show an example embodiment of fluid transfer with an example embodiment of a fluidic unit according to the present disclosure;

FIGS. 11A to 11C show an example embodiment of fluid transfer with an example embodiment of a fluidic unit according to the present disclosure;

FIGS. 12A to 12C shows the designs of example embodiments of fluidic units according to the present disclosure;

FIGS. 13A to 13E show an example embodiment of fluid transfer with an example embodiment of a fluidic unit according to the present disclosure;

FIGS. 14A to 14F show example embodiments of fluidic units with reagents according to the present disclosure;

FIGS. 15A to 15C show example embodiments fluidic units with filter membranes according to the present disclosure;

FIG. 16 shows an example embodiment of a fluidic circuit according to the present disclosure;

FIG. 20A to 20C show example embodiments of fluidic circuits according to the present disclosure;

FIGS. 21A to 21C show example embodiments of fluidic units with a plurality of layers according to the present disclosure;

FIGS. 22A to 22C show example embodiments of fluidic units with a plurality of layers according to the present disclosure;

DETAILED DESCRIPTION

Figure 1:
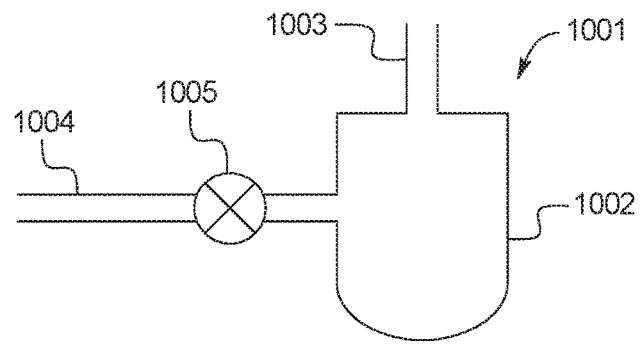
FIG. 1 shows the design of an example embodiment of a fluidic unit according to the present disclosure.

FIG. 1 shows the design of a fluidic unit 1001, which comprises a chamber 1002, a venting port 1003 and a microfluidic channel 1004 that is in fluid communication with and accesses the chamber and includes a passive valve 1005. The fluidic unit can be used to handle different fluids, such as liquid, liquid containing bubbles, or liquid containing particles. The fluids can be body fluids (e.g. blood, urine, saliva, etc.), reagent solutions, beads suspended in buffer, etc.

The fluidic chamber 1002 provides an enclosed space to receive and store fluid. Fluidic chamber 1002 is designed so that the fluid can sink or be pulled down to the bottom of the chamber and bubbles can float up to the top, either by gravity or other forces such as a pneumatic or centrifugal force. One way to achieve this property is to have fluidic chamber 1002 dimensioned large enough so that the gravity is more dominant than the surface tension of the fluid. It can also be achieved in other ways, for example, by applying a centrifugal force more dominant than the surface tension. A preferred dimension of fluidic chamber 1002 is 0.1 mm to 50 mm in width, 0.1 mm to 50 mm in depth, and 0.1 mm to 100 mm in height. Fluidic chamber 1002 could be any shape, for example, cuboid, cylindrical, spherical or other shapes of containers known to persons skilled in the art, with dimensions in the above ranges.

The venting port 1003 is configured to apply pneumatic pressure to fluidic chamber 1002. Venting port 1003 should be positioned above the fluid when the device is in use. Venting port 1003 can be below the fluid when the device is in storage or other states of nonuse. It can be of any size and of any surface property. Preferably, venting port 1003 is a micro-sized channel with a hydrophobic surface, where surface tension is more dominant than gravity. The pneumatic pressure applied to the venting port 1003 can be of atmosphere pressure, a pressure higher than the atmosphere, or a vacuum lower than the atmosphere. When the venting port 1003 is connected to an atmosphere pressure, it can act as a pressure buffer to keep the pressure inside the chamber constantly equalized to atmosphere.

Figure 2A:
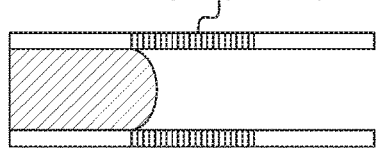
FIGS. 2A to 2D show example embodiments of passive valves that can be used with the fluidic unit of FIG. 1.
Figure 2B:
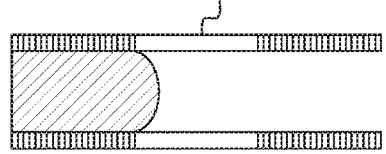
Figure 2C:
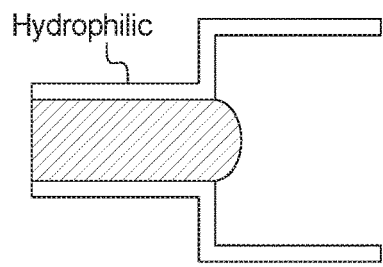
Figure 2D:
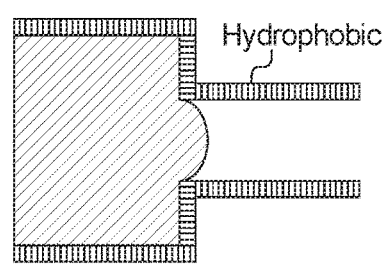

The microfluidic channel 1004 is in fluid communication with and accesses the enclosed space of fluidic chamber 1002. Preferably, microfluidic channel 1004 is a micro-sized channel where surface tension is more dominant than gravity. In an embodiment, microfluidic channel 1004 has a cross section of 0.1 um to 5 mm in width and 0.1 um to 5 mm in depth. The cross section can be in shape of a rectangle, a trapezoid, a cylinder or any other shapes known to persons skilled in the art. Additionally, microfluidic channel 1004 includes a passive valve 1005, which stops fluid flow if the pressure difference across the fluid meniscus is below a designated threshold $\Delta P$. The positioning of valve 1005 is preferably close to the chamber, so that the fluid volume between the valve and the chamber is negligible in comparison to the fluid volume being manipulated. In example embodiment, passive valve 1005 can be a hydrophobic patch (FIG. 2A), a hydrophilic patch (FIG. 2B), a sudden diameter enlargement of a hydrophilic channel (FIG. 2C), a sudden diameter shrink of a hydrophobic channel (FIG. 2D), or other designs that are known to person skilled in the art. In the dimension range of the microfluidic channel, surface tension of the fluid is more dominant than the inertia force such as gravity.

Figure 3:
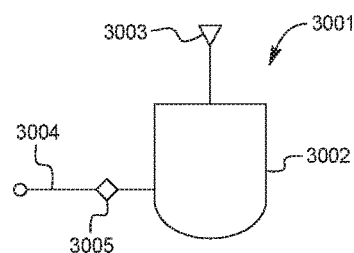
FIG. 3 shows the design of an example embodiment of a fluidic unit according to the present disclosure.

To simplify the drawings, a design symbol 3001 as shown in FIG. 3 is used to represent the fluidic unit, with a fluidic chamber 3002, a venting port 3003, a microfluidic channel 3004, and a passive valve 3005. Two threshold pressures are associated with the passive valve, $\Delta P_{in}$ in the direction of fluid entering the chamber and $\Delta P_{out}$ in the direction of fluid leaving the chamber. The threshold pressures can be of any value, as discussed below:

$\Delta P_{in}>0, \Delta P_{out}=0$: One-way valve for stopping flow into chamber [1]

$\Delta P_{in}=0, \Delta P_{out}>0$: One-way valve for stopping flow out of chamber [2]

$\Delta P_{in}>0, \Delta P_{out}>0$: Two-way valve [3]

$\Delta P_{in}=0, \Delta P_{out}=0$: valve provide no pressure barrier [4]

Figure 4A:
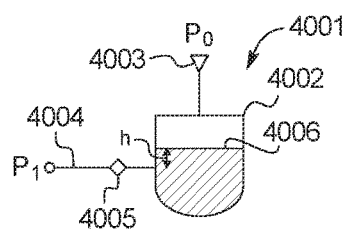
FIGS. 4A to 4I show an example embodiment of fluid transfer with an example embodiment of a fluidic unit according to the present disclosure.
Figure 4C:
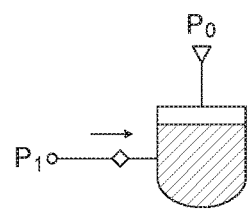

In operation, two states of the fluidic units should be considered. State 1: the channel 4004 is beneath the fluid (h≥0), as shown in FIG. 4A. State 2: the channel 4004 is above the fluid (h<0), as shown in FIG. 4B. The parameter h represents the height difference from a fluid surface 4006 to the microfluidic channel.

When storing fluid in a chamber 4002 without flow, as shown in FIG. 4A (h>=0) and FIG. 4B (h<0), the pressure difference between a venting port 4003 ($P_0$) and the microfluidic channel ($P_1$) should satisfy that:

$-\Delta P_{in}-\rho gh \leq P_0-P_1 \leq \Delta P_{out}-\rho gh$, if $h \geq 0$ [5]

$P_1-P_0 \leq \Delta P_{in}$, if $h<0$ [6]

where $\rho gh$ is the hydraulic pressure of the fluid. To transfer fluid into the chamber, as shown in FIG. 4C (h>=0) and FIG. 4D (h<0), the pressure difference should satisfy that:

$P_1-P_0>\Delta P_{in}+\rho gh$, if $h \geq 0$ [7]

$P_1-P_0>\Delta P_{in}$, if $h<0$ [8]

Figure 4E:
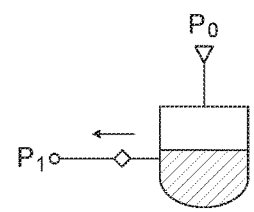
Figure 4B:
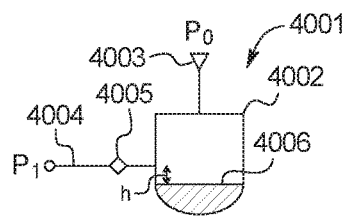
Figure 4D:
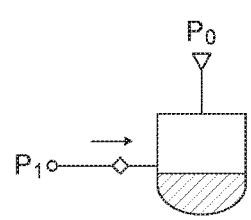

To transfer fluid out of the chamber, as shown in FIG. 4E (h>=0), the pressure difference should satisfy that:

$P_0-P_1>\Delta P_{out}-\rho gh$, if $h \geq 0$ [9]

Figure 4F:
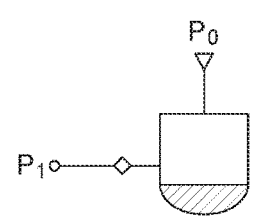
Figure 5A:
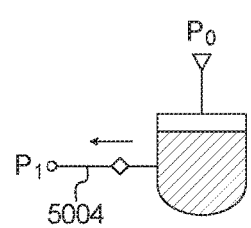
FIGS. 5A and 5B show an example embodiment of fluid transfer with an example embodiment of a fluidic unit according to the present disclosure.
Figure 5B:
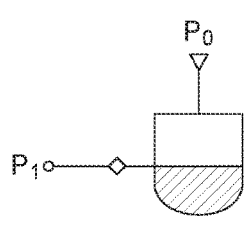

No fluid would be transferred out of the chamber in State 1 (h<0), as shown in FIG. 4F, by applying the pressure difference ($P_0-P_1$). This property can be utilized as a "self-stop" mechanism, as shown in FIG. 5. The fluid in the chamber is initially above the microfluidic channel 5004, as shown in FIG. 5A, and is transferred out of the chamber by applying the pressure difference ($P_0-P_1$). When the fluid level falls to the height of the channel 5004, as shown in FIG. 5B, the fluid transfer is stopped automatically, without the need of accurate timing to remove the pressure difference ($P_0-P_1$). This "self-stop" mechanism helps to solve the challenge of accurate volumetric control in pneumatically actuated cartridges. Nevertheless, the chamber can be tilted until that channel 5004 is below the fluidic (from state 2 h<0 into stage 1 h>0) to enable the fluid being further transferred out if needed.

Table 1 summarizes the operations of the fluidic unit.

TABLE 1

Pressure difference ($P_0 - P_1$) to actuate the fluidic transfer.

| State | No Flow | In Flow | Out Flow |
|---|---|---|---|
| h ≥ 0 | $-\Delta P_{in} - \rho g h \leq P_0 - P_1 \leq \Delta P_{out} - \rho g h$ | $P_0 - P_1 < -\Delta P_{in} - \rho g h$ | $\Delta P_{out} - \rho g h < P_0 - P_1$ |
| h < 0 | $P_0 - P_1 \geq -\Delta P_{in}$ | $P_0 - P_1 < -\Delta P_{in}$ | No out flow for any ($P_0 - P_1$) |

The pneumatic pressure $P_0$ applied to the venting port can be adjusted independently, for example, by an external pressure source such as atmosphere pressure or an internal source such as a pressure controller. The pressure in the microfluidic channel $P_1$ can be dependent on several factors, including the hydraulic pressure propagation along the fluid and air in the channel, flow resistance of the channel, the surface tension force (fluid versus channel wall interface, fluid versus air interface, and fluid versus another fluid with different surface tension, etc.), and pneumatic pressure applied by an external or internal pressure source, etc. In certain embodiments, the venting port is kept free of fluid. In certain embodiments, the microfluidic channel can be fully filled of fluid, partially filled of fluid, or free of fluid.

In an embodiment, a device containing a fluidic cartridge with the above fluidic units or a device containing the above fluidic units can include a controller configured to control pressures applied to the fluidic units above, for example, by controlling a pneumatic force applied to the fluidic chamber via a venting port. In an embodiment, the controller is configured to control the pneumatic pressure such that In Flow, Out Flow, or No Flow occurs according to the equations above. For example, the controller can control a pneumatic force applied at a venting port to cause $P_0$ to change to satisfy the above equations and cause the In Flow, Out Flow, or No Flow conditions.

Figure 4G:
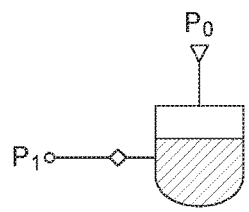
Figure 4H:
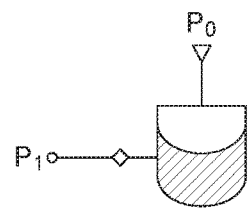
Figure 4I:
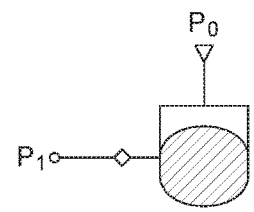

Due to surface tension, the fluid stored in the chamber may have a flat top surface, such as shown in FIG. 4G, or a non-flat top surface, such as shown in FIG. 4H and FIG. 4I. The fluidic unit works for both scenarios. Correction can be made by measuring the surface profile to compensate the fluid volume accuracy. In other embodiments, chemicals such as surfactant can be added to the fluidic to modify the surface tension of the fluid, and thus also change the fluidic surface profile.

FIG. 6 and FIG. 7 show two examples of implementing the fluidic unit. FIG. 6 shows an application of removing bubbles. As illustrated, a fluid containing bubbles is transferred into the unit, as shown in FIG. 6A. And after entering the chamber, the bubbles float up and burst as shown in FIG. 6B, due to the floating force introduced by gravity or a replacement force such as centrifugal force. To accelerate the bubble removal, a pneumatic vacuum lower than the gas pressure inside the bubbles can be applied to the venting port. The fluidic unit can be used in a cartridge to remove bubbles in an initial biological sample, for example, undesirable bubbles in finger-prick blood. The fluidic unit can also be used to remove bubbles induced in the cartridge, for example, bubbles from thermal cycles of a Polymerase Chain Reaction (PCR).

FIG. 7 shows the application of accelerating fluid mixing. As illustrated, two fluids are received in the unit, as shown in FIG. 7A. To accelerate mixing, gas (e.g. air) is pumped into fluid to induce chaotic flow, as shown in FIG. 7B. Proper mixing can be quickly achieved with this operation. Upon the completion of mixing, bubbles can leave the fluid as shown in the examples of FIG. 6.

In an embodiment, a device containing a fluidic cartridge with the above fluidic units or a device containing the above fluidic units can include a controller configured to control the above fluid mixing.

Design of Fluidic Unit with Variations

The design of the fluidic unit can be modified to have a plurality of variations. In an embodiment, the microfluidic channel can be at different positions with respect to the chamber, as shown in FIGS. 8A-C. In another embodiment, the microfluidic channel can be either perpendicular or non-perpendicular to the chamber sidewall, as shown in FIG. 8D. In yet another embodiment, the microfluidic channel can have a bend, instead of being a straight channel, as shown in FIG. 8E. In another embodiment, the fluidic unit can have two or more of microfluidic channels, as shown in FIG. 8F. In another embodiment, there can be more than one passive valve in one fluidic channel that is accessing the chamber. The fluidic unit can have a plurality of the above variations and/or combinations thereof.

Figure 8G:
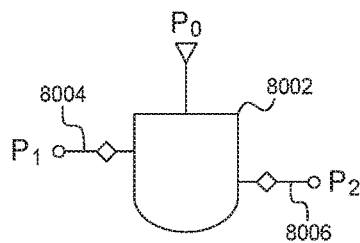

For fluid units with more than one microfluidic channel accessing the chamber, the operation of each of the channel can be considered versus the venting port, such as described in Table 1. Meanwhile, the pressure in each of channel is not fully independent from each other, but rather coupled by hydraulic pressure of the fluid and air inside the chamber and the channel. For example, as shown in FIG. 8G, two microfluidic channels 8004 and 8006 are both accessing chamber 8002 and there is no fluid in the chamber. In this scenario, P1 and P2 are coupled by hydraulic pressure of the air inside the chamber and the channel. When there is a pressure difference between P1 and P2, airflow will be generated between these two channels and balance the pressure difference against the flow resistance of the chamber and the channel.

Figure 8H:
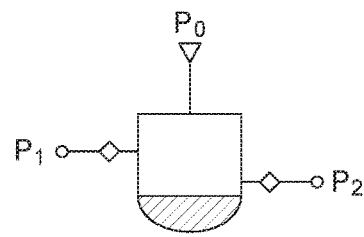

In another example, as shown in FIG. 8H, two microfluidic channels P1 and P2 are both accessing the chamber, and the fluid in the chamber is below the height of the channels. In this scenario P1 and P2 are coupled in the same way as in the example of FIG. 8G.

Figure 8I:
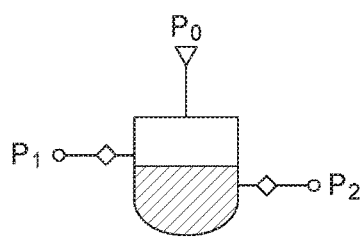

In another example, as shown in FIG. 8I, two microfluidic channels P1 and P2 are both accessing the chamber, and the fluid in the chamber is below the height of one channel and above the height of the other channel. In this scenario, P1 and P2 are coupled by the hydraulic pressure of both the air and the fluid (P1 to chamber by air, P2 to chamber by fluid). When there is pressure difference between P1 and P2, air and/or fluid flow is generated between the two channels, and the pressure difference is balanced again the flow resistance of the fluid and/or air.

Figure 8J:
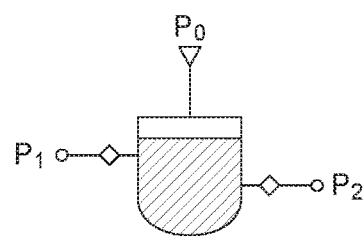

In another example, as shown in FIG. 8J, two microfluidic channels P1 and P2 are both accessing the chamber, and the fluid in the chamber is below the height of both the two channels. In this scenario, P1 and P2 are coupled by the hydraulic pressure of the fluid. When there is pressure difference between P1 and P2, fluid flow is generated between the two channels, and the pressure difference is balanced against the flow resistance of the fluid.

As a force such as gravity is pulling the fluid towards the bottom the unit, thus no fluid flow is generated into the venting port. Thus, the pressure difference between the pneumatic pressure applied at the venting port versus the pneumatic pressure in the chamber is balanced by airflow resistance which can be controlled to be relatively minimal.

Figure 9A:
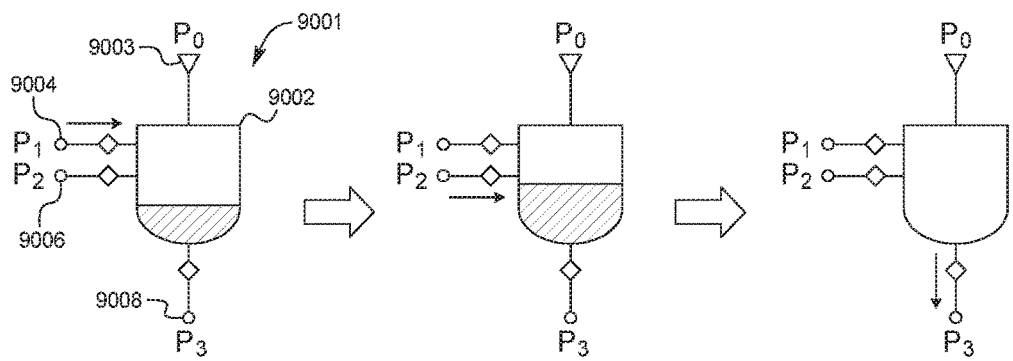
FIGS. 9A and 9B show an example embodiment of fluid transfer with an example embodiment of a fluidic unit according to the present disclosure.
Figure 9B:
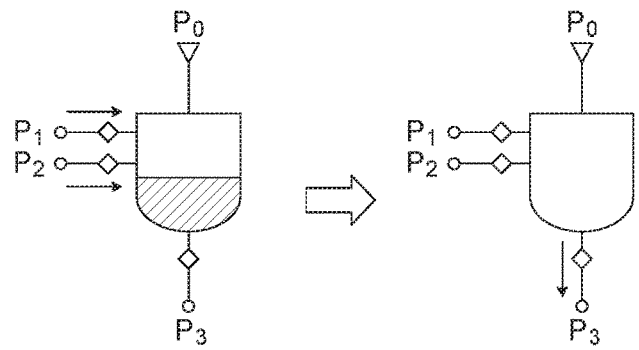

In fluidic units that have two or more of the microfluidic channels, fluid transfer in each of the channels can be carried out in serial, in parallel, or in a combination of both. For example, FIG. 9 shows a fluidic unit that has three microfluidic channels 9004, 9006 and 9008. In FIG. 9A, the fluid transfer in these three channels is carried out in serial. More specifically, in Step 1, a fluid is transferred into the unit via the channel 9004. In Step 2, a fluid is transferred into the unit via the channel 9006. In Step 3, the fluid in the unit is transferred out via the channel 9008. In FIG. 9B, the fluid transfer via the channel 9004, 9006 and 9008 is a combination of both in serial and in parallel. In Step 1, fluid transfers via the channel 9004 and 9006 are carried out in parallel. In Step 2, fluid transfer via the channel 9008 is carried out in serial to the previous step.

FIG. 10 shows an example of a fluidic unit 10001 to mix fluids. First, one fluid 10010 is transferred into the unit via a channel 10004, as shown in FIG. 10A, and another fluid 10011 is transferred into the unit via a channel 10006, as shown in FIG. 10B. The two fluids can be mixed by diffusion, as shown in FIG. 10C, or by the accelerated mixing with bubbles, as shown in FIG. 10D.

FIG. 11 shows an example of using a fluidic unit to transfer fixed volumes of fluid with the "self-stop" mechanism discussed above. As shown in FIG. 11A, a fluid volume $V_0$ can be transferred out a channel 11004. The volume $V_0$ is determined by the initial fluid level and the height of the channel 11004 with respect to the fluid chamber, and does not rely on timing of the pneumatic actuation. As shown in FIG. 11B, a fluid volume $V_1$ can then be transferred out from a channel 11006. The volume $V_1$ is determined by the height difference of the two channels 11004 and 11006. In an embodiment, as shown in FIG. 11C, a microfluidic channel 11008 can be positioned at the bottom of the chamber to transfer a fluid volume $V_2$, which is dependent on the position of channel 11006, to fully drain the unit. In other embodiments, the fluidic unit can have more of the microfluidic channels to transfer a series of fixed fluid volumes.

FIG. 12 shows examples for flow relay. FIG. 12A shows a unit for flow relay with two inlet channels 12004 and 12006 and one outlet channel 12008. Fluid flow can be sent from 12004 into the chamber and then drained out of the chamber by channel 12008. Fluidic flow can also be sent from 12006 into the chamber and then drained by channel 12008. In this way, two fluid flows (one from 12004 to 12008 and one from 12006 to 12008) can be carried out separately and in sequential, but both using 12008 as outlet. Similarly, FIG. 12B shows a fluidic unit for flow relay with one inlet channel 12014 and two outlet channels 12016 and 12018. Fluid flow from channel 12014 to channel 12016 can be carried out separately and in sequential versus fluid flow from channel 12014 to channel 12018. FIG. 12C shows a unit for flow relay from two inlet channels 12024 and 12026 to two outlet channels 12028 and 12030. Fluid flow can be carried out separately and in sequential from either one of the two inlet channels 12024 and 12026, into either one of the two outlet channels 12028 and 12030. The operation of flow relay can be repeated more than once in the above units. In other embodiments, there can be any combination of more than one of the fluid inlet and more than one of the fluid outlets.

FIG. 13 shows a schematic view for washing particle suspensions in fluid. Washing is a step frequently used in flow cytometer, molecular diagnostics and other biological analysis to purified cells, beads or other particles in a fluid sample. FIGS. 13A-D show an example embodiment of washing particles with a density higher than fluid. First, a fluid 13001 with particle suspensions is transferred into the chamber, as shown in FIG. 13A, and the particles 13002 are allowed to sediment to the bottom of the chamber, as shown in FIG. 13B. The excessive fluid is then drained away via a channel 13016 that is above the particle sedimentations, as shown in FIG. 13C. Afterwards, a wash buffer 13003 can be transferred into the chamber to re-suspend the particles, as shown in FIG. 13D. These four steps can be repeated as needed to further purify the particles. For particles 14004 that have lower density than the fluid, as shown in FIG. 13E, they are allowed to float up in the unit. The excessive fluid is drained away via a channel 14018 that is below the floating particles, on the bottom surface of the chamber. The sedimentation or floating of the particles can be accelerated by centrifugation, magnetic field, acoustic waves or other methods that are known to person skilled in the art.

The fluidic unit can also have other variations. For one example, the unit can be initially supplied with reagents in the chamber, as shown in FIG. 14. The regents can be fluid as shown in FIG. 14A, solid beads as shown in FIG. 14B, and/or a fluid of bead suspensions as shown in FIG. 14C. The reagents can also be a dried film coating, as shown in FIG. 14D, dried powders as shown in FIG. 14E, dried blocks as shown in FIG. 14F, or any other format. As such, the fluid transferred into the fluidic unit can mix and react with the reagents to facilitate further analysis. In an embodiment, the reagents are stored in the chamber prior to the introduction of fluid into the chamber.

In yet other variations, additional features can be added to the unit. FIG. 15A shows the example of a filter membrane 15008 added to the chamber of the unit. Filter membrane 15008 is helpful for the washing process, as described in FIG. 13, and also for other process, such as separating particles from a fluid. By picking a filter with pore size smaller than target particles 15001, as shown in FIG. 15B, the filter can trap the particles and allow fluid to flow through, which is useful in biological tests, for example, in separating plasma from a whole blood sample. In other embodiments, filter membrane 15008 can be in different orientations, such as in a vertical orientation as shown in FIG. 15C. In yet other embodiments, the fluidic unit can have more than one filter membrane to capture different target particles (e.g. different size).

In an embodiment, a device containing a fluidic cartridge with the above fluidic units or a device containing the above fluidic units can include a controller configured to control fluid flow through the above fluidic units, for example, by controlling a pneumatic force applied to a fluidic chamber via a venting port or by controlling pumps an/or valves in fluid communication with microfluidic channels of the fluidic units.

Fluidic Circuits with a Plurality of Units

A plurality of the above described fluidic units can be used together to form fluidic circuits for different functions. The fluidic units can be used in serial, in parallel, or in a combination of both, and connected with other fluidic circuits. In a preferred embodiment of the fluidic circuit, any two fluidic units in the circuit are interconnected with no more than one fluidic conduct. In others embodiments of the fluidic circuit, there could be more than one fluidic conduct interconnecting two fluidic units in the circuit. When a plurality of the units is used in the circuits, it is useful that the venting ports of the chamber in each unit are controlled independently. For example, if one venting port is controlled to be connecting with the atmosphere, the pressure in the chamber is then constantly equalized to the atmosphere pressure (or having minimal pressure difference). In this way, pressure propagation along fluid and/or air can be decoupled from unit to unit, which simplifies the operation of the fluid circuit.

Figure 17A:
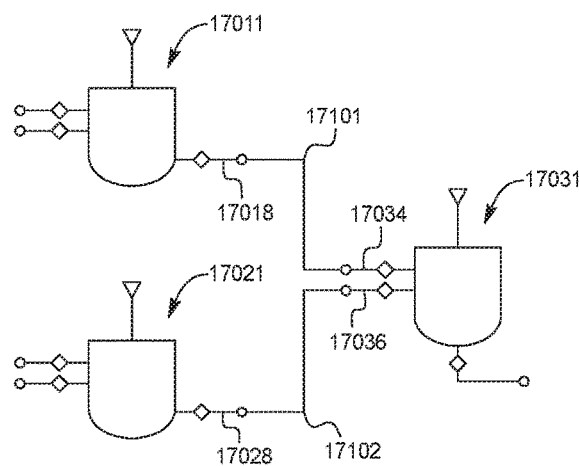
FIGS. 17A and 17B show example embodiments of a fluidic circuits according to the present disclosure.
Figure 17B:
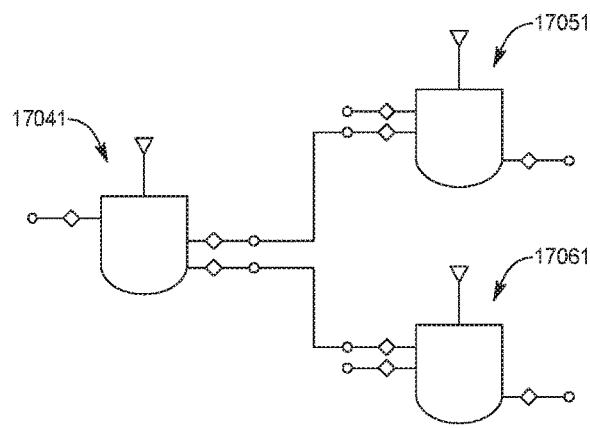
Figure 18:
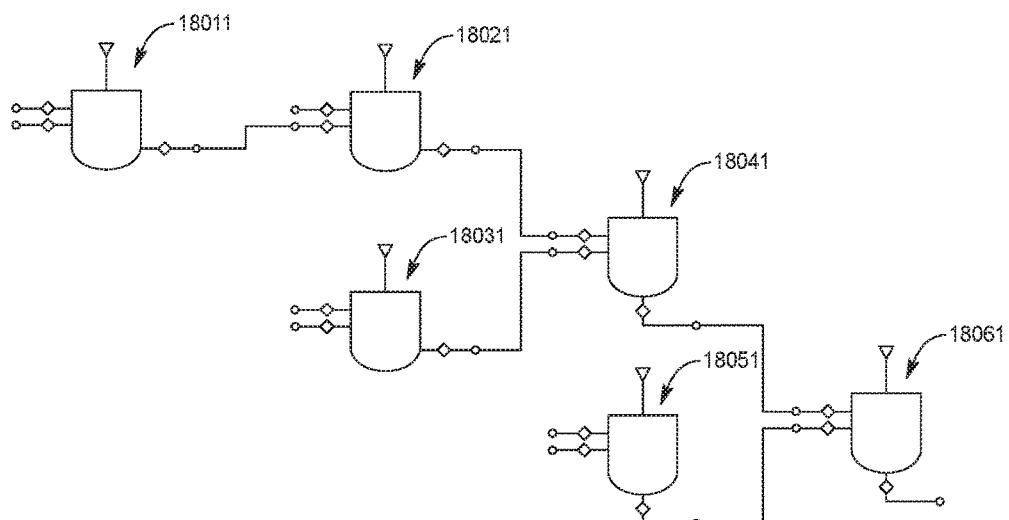
FIG. 18 shows an example embodiment of a fluidic circuit according to the present disclosure.
Figure 19A:
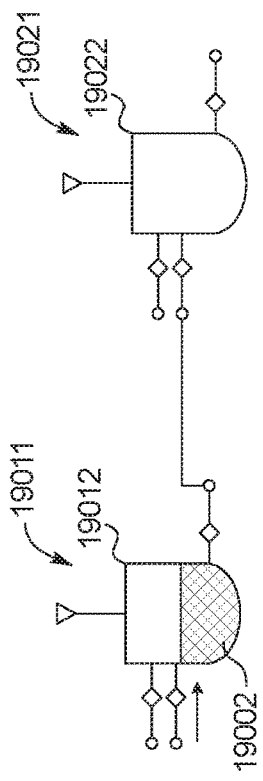
FIGS. 19A to 19D show an example embodiment of fluid transfer with an example embodiment of a fluidic circuit according to the present disclosure.
Figure 19B:
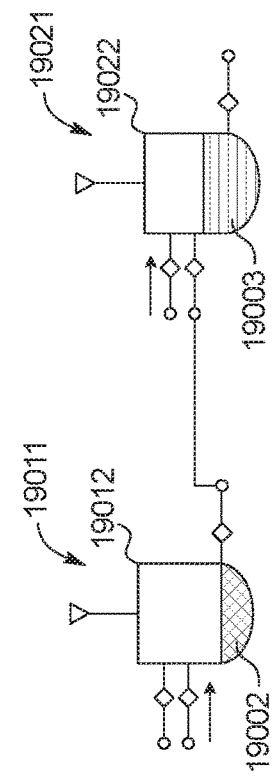
Figure 19C:
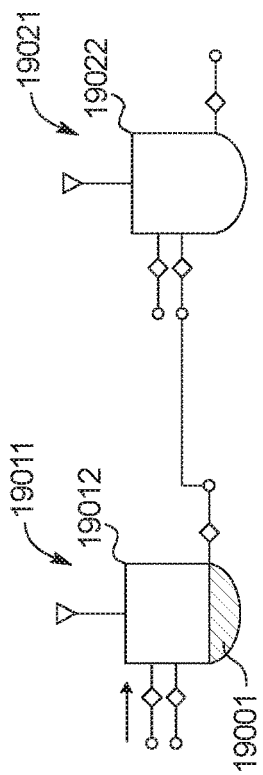
Figure 19D:
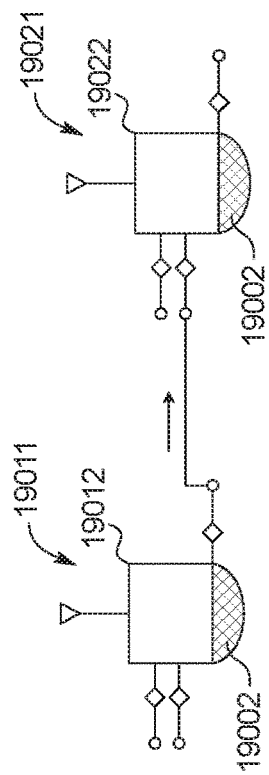

FIG. 16 shows an example of a fluidic circuit with two fluidic units 16011 and 16021 in a serial configuration. A fluid conduit 16101 connects channel 16018 of the unit 16011 with channel 16026 of unit 16021. FIG. 17A shows an example embodiment of a fluidic circuit with two fluidic units 17011 and 17021 in a parallel configuration, which are connected to a third fluidic unit 17031 in a serial configuration. FIG. 17B shows another example embodiment of a fluidic circuit with a first fluidic unit 17041 in serial to two fluidic units 17051 and 17061 that are in a parallel configuration. In other embodiments, there can be more fluidic units in the fluidic circuits. FIG. 18 shows one example embodiment of a fluidic circuit with six of fluidic units. Giving the design of the basic fluidic unit and its operation roles, designing more complex circuits can be achieved by a person skilled in the art.

FIG. 19 shows an example embodiment of a fluidic circuit for serial dilution. The function of serial dilution is frequently used in biological tests such as Complete Blood Count and ELISA assays. The fluidic circuit has two units 19011 and 19021 in a serial configuration. FIG. 19A shows a fluid sample 19001 transferred into the unit 19011. In FIG. 19B, a first diluent is then transferred into the unit 19011 via a same or separate fluid channel and mixes with the initial sample in chamber 19012 to form a once-diluted sample 19002. Thereafter, a fixed volume of the once-diluted sample 19002 is transferred into a second fluidic chamber 19022 of fluidic unit 19021, as shown in FIG. 19C. Finally, a second diluent is transferred into fluidic unit 19021 to mix with once-diluted sample 19002 and form a twice-diluted sample 19003, as shown in FIG. 19D. In other embodiments, a fixed volume of the twice-diluted sample 19003 can be transferred into following units for further dilution.

T-junctions, which are intersections of fluidic channels, can be used with the presently disclosed microfluidic designs. For example, FIG. 20A shows a T-junction 20104 that is formed by the intersection of three fluidic conduits 20101, 20102 and 20103. However, T-junctions face the complexity of pressure balance, so it is preferable to avoid T-junctions. The fluidic unit of the present disclosure can be used to replace T-junctions, either in cartridges discussed in the present disclosure or in other microfluidic cartridges. FIG. 20A shows an example embodiment of using a fluidic unit 20031 to replace the T-junction 20104 in FIG. 20A. Fluidic unit 20031 acts as a flow relay, as described in FIG. 12, to transfer fluid among the three fluidic conducts 20101, 20102 and 20103 separately. In other embodiments, as shown in FIG. 20B, T-junctions formed by intersections of more than three channels can be replaced by the fluidic unit. In yet other embodiments, multiple T-junctions can be formed in cascade, as shown in FIG. 20C. In an embodiment, fluidic units can be used to replace each of the intersections of FIG. 20C.

In an embodiment, a device containing a fluidic cartridge with the above fluidic units or a device containing the above fluidic units can include a controller configured to control fluid flow through the above fluidic units, for example, by controlling a pneumatic force applied to a fluidic chamber via a venting port or by controlling pumps an/or valves in fluid communication with microfluidic channels of the fluidic units.

Structure of the Fluidic Units

The fluidic units of the present disclosure can be formed with a plurality of layers. For example, a fluidic unit can be formed with a two-layer structure, as shown in FIG. 21. FIG. 21A shows the side view of a basic fluidic unit, and FIG. 21B shows the cross-sectional view of the two-layer structure. In this example embodiment, a first layer 21001 has cavity structures, and a second layer 21012 is a flat substrate. These two layers bond together to form the fluidic channels and chambers of the unit. The passive valve 21013 of this example is formed with a sudden enlargement of the channel geometry and hydrophobic treatment of the surface property locally. The venting port 21003 can be a through hole in the first layer 21001, an opening in the sidewall of the first layer 21001, or a through hole in the second layer 21012. The venting port can access the chamber directly or indirectly via a fluidic channel connecting to the chamber.

In other embodiments, the first layer 21011 can be formed of materials such as thermoplastics (e.g. acrylic, polycarbonate, polyethylene, etc.), silicone, parylene, or other materials such as polymer, plastic, glass, silicon, or other materials known to those skilled in the art of fluidics. The cavities of the first layer 21011 can be formed with manufacturing process such as injection molding, compression embossing, 3D printing, CNC, etching, or other process that are known to those skilled in the art. In further embodiments, the second layer 21012 can be a rigid piece or a flexible membrane. The rigid piece can be of same material as the first layer or a different material. In an example embodiment, the membrane can be a plastic film. In another example embodiment, the membrane can be a plastic film laminated with an aluminum foil. For embodiments with a membrane as the second layer 21012, the membrane can be pierced open during operation of the cartridge. For example, the venting ports can be sealed with the membrane initially and pierced open during operation.

In other embodiments, the second layer 21012 can also have cavities. As illustrated in FIG. 21C, the fluidic channels and chambers can be formed by any of the following combinations: cavities in the first layer 21011 with a flat portion of the second layer 21012, cavities in the second layer 21012 with the flat portion of the first layer 21011, and cavities in the first layer 21011 with cavities in the second layer 21012. The terms "first" and "second" are referring to the top and bottom layers in the drawing and can be used interchangeably. In some embodiments, at least one layer can be transparent for optical observations and measurements.

A fluidic unit according to the present disclosure can also be embodied in a three-layer structure, as shown in FIG. 22. A middle layer 22003 can be added in between the first layer 22001 and the second layer 22002. The middle layer 22003 can cover at least a portion part of the interface between the first and second layers. In some embodiments, the middle layer 22003 can be a structure layer with cavities, so that multiple layers of fluidic channels and chambers can be formed, as shown in FIG. 22A. In another embodiment, the middle layer 22003 can be a membrane, which for example can seal reagents in the fluidic chambers and can be pierced open during operation, as shown in FIG. 22B. In another embodiment, the middle layer 22003 can be a metal electrode, the surface of which can be treated to use as one or more sensors. In other embodiments, as shown in FIG. 22C, the middle layer 22003 can be a mesh structure to form the filter membrane described in FIG. 15.

Embodiments for Biological Tests: Complete Blood Count

Fluidic circuits including a plurality of the fluidic unit can be used together to form a cartridge for one or more biological tests. Fluidic circuits can also include other fluidic components to form the cartridges. These components can include but not limit to fluidic channels, sample retaining chamber, pumps, valves, flow sensors, or any other component that is known to person skilled in the art. Certain embodiments of the fluidic cartridge can be used for cell analysis in biological samples, such as a Complete Blood Count (CBC). A CBC analysis comprises four parts, including analysis of the white blood cells (WBCs), the red blood cells (RBCs), the platelet cells (platelets) and the hemoglobin.

Figure 23A:
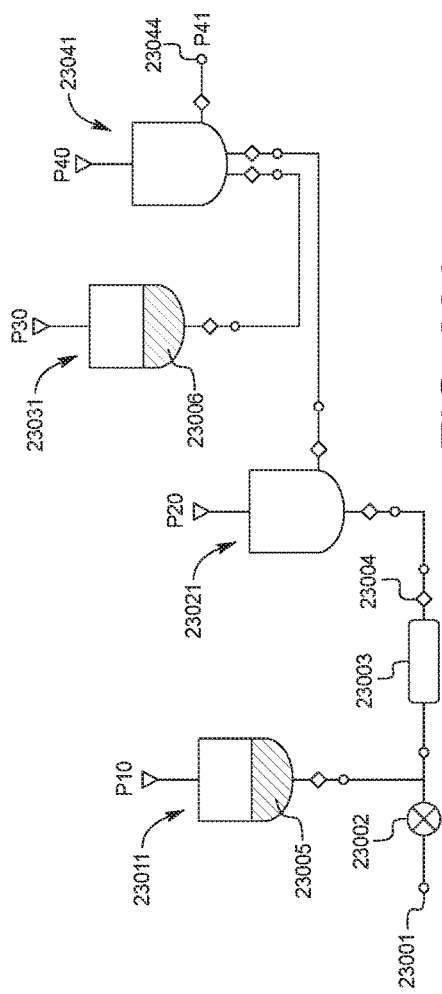
FIG. 23A shows an example embodiment of a fluidic circuit according to the present disclosure.

FIG. 23A shows a fluidic cartridge for a CBC analysis. The fluidic circuit has four fluidic units 23011, 23021, 23031 and 23041. The fluidic units 23011 and 23031 are initially loaded with reagent solutions 23005 and 23006, respectively. To operate the fluidic circuits, in Step 1, a blood sample is introduced through inlet port 23001, drawn into the sample-retaining chamber 23003 by capillary force, and stopped at capillary break 23004. The volume of the blood sample can be determined based on the geometry of the retaining chamber. In Step 2, valve 23002 is closed to seal off the inlet port 23001. In Step 3, the first reagent 23005 is transferred out of the unit 23011, flushing the blood sample in retaining chamber 23003 into fluidic unit 23021 for mixing. The volume of the reagent 23005 can be determined with the known volume stored in the unit, or with other methods such as the function of fixed volume transfer as shown in FIG. 11. The mixing of the blood sample with the reagent 23005 can be accelerated by pumping air bubbles, and forms a once-diluted sample in fluidic unit 23021. In Step 4, a fixed volume of the once-diluted sample is transferred into fluidic unit 23041. In Step 5, the second reagent 23006 is transferred into fluidic unit 23041, where it mixes the once-diluted sample and forms a twice-diluted sample. In step 6, a fixed volume of the twice-diluted sample can be transferred out of the channel 23044 for downstream analysis.

In some embodiments, the biological sample can be whole blood, and both the first reagent 23005 and the second reagent 23006 are isotonic diluents. In this embodiment, the twice-diluted sample can be used for achieving various dilution ratios of the blood sample, such as dilution ratio of 1:10 to 1:10,000, for the purpose of analysis of WBC, RBCs and platelets in CBC. The serial dilution of two times is used to achieve a high dilution ratio with a lesser diluent volume. In other embodiments, a one-time dilution with one unit can be used. In other embodiments, a serial dilution with more than two units can be used. In another embodiment, the first reagent 23005 can be a non-isotonic diluent, and the second reagent 23006 can be a WBC labeling reagent. In this embodiment, the once-diluted sample can have RBCs lysed for hemoglobin analysis. The twice-diluted sample can be used for WBC analysis downstream.

Figure 23B:
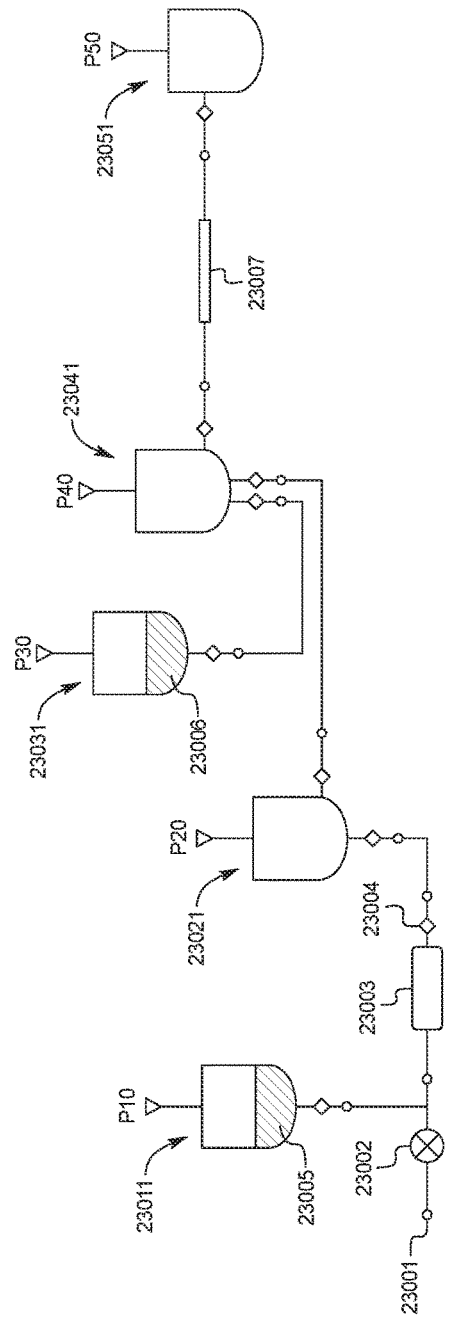
FIG. 23B shows an example embodiment of a fluidic circuit according to the present disclosure.

FIG. 23B shows an example of the above cartridge with a sheathless, microfluidic channel 23007 to perform the cytometer analysis of the WBCs, RBCs and platelets. The inner diameter of the sheathless channel 23007 should be larger than target cells for analysis, and be small enough to minimize coincidence error, i.e. the possibility of multiple cells overlapping. When the diluted sample flows through channel 23007, individual cells can be measured by methods such as optical sensing in flow cytometry, impedance sensing or any other measurement methods that are known to those skilled in the art. After analysis, the residual sample can be transferred into fluidic unit 23051 as a waste reservoir. With this cartridge device, the total count of WBCs, RBCs and platelets, and the cell indices including but not limited to mean corpuscular volume (MCV), Mean Corpuscular Hemoglobin (MCH), Mean Corpuscular Hemoglobin Concentration (MCHC), and WBC properties including but not limited to WBC differential (e.g. lymphocyte, monocyte, neutrophil, eosinophil and basophil), can be measured from the blood sample.

Figure 24:
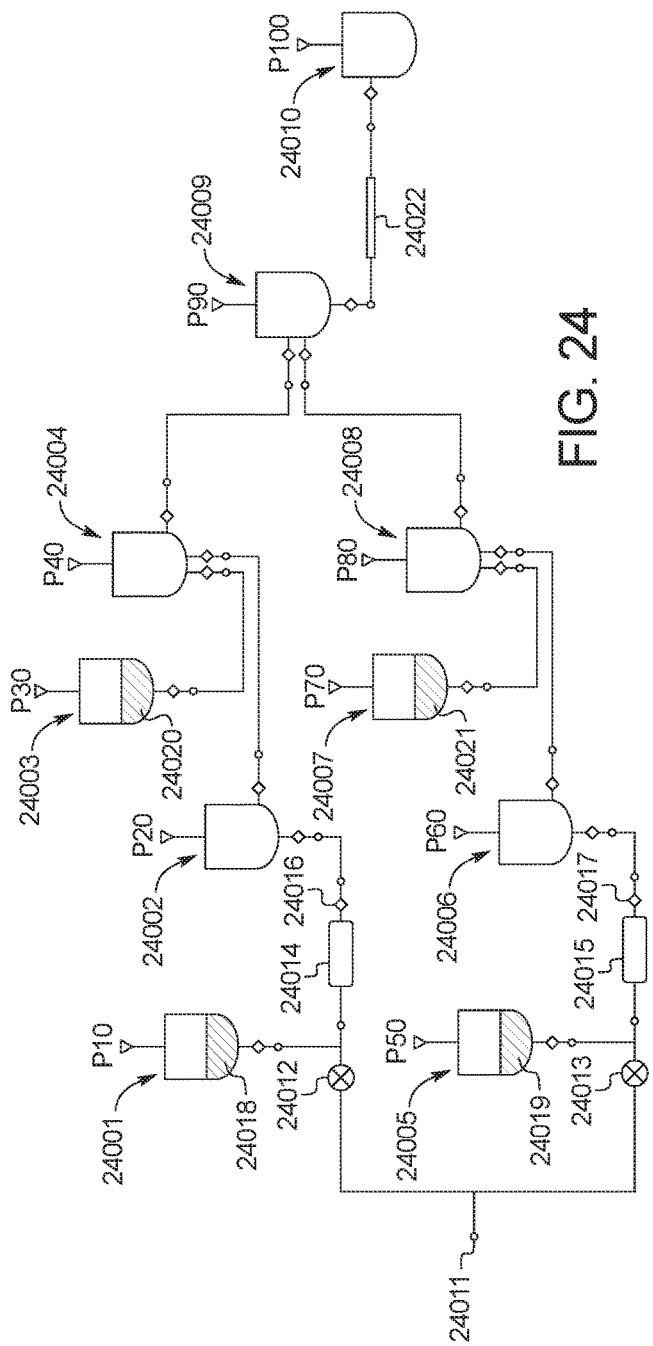
FIG. 24 shows an example embodiment of a fluidic circuit according to the present disclosure.

FIG. 24 shows one embodiment of a cartridge that integrates the whole CBC panel. This cartridge includes two duplicates of the cartridge in FIG. 23A. Additional features are added to run the two components of the CBC panel: first, the WBC and hemoglobin analysis, and second, the RBC and Platelet analysis, in one cartridge. One feature is a common inlet port 24011 to draw a blood sample simultaneously into two retaining chambers 24014 and 24015, which are used for the RBC/Platelet analysis and WBC/Hemoglobin analysis, respectively. Another feature is a fluidic unit 24009 as flow relay to direct the twice-diluted samples into one sheathless channel 24022 for the cytometer analysis separately. In other embodiments, additional CBC parameters can also be measured, such as Reticulocyte count, Nucleated RBC count, Platelet aggregates, etc. by modifying the reagents stored in the cartridge.

In an embodiment, a device containing a fluidic cartridge with the above fluidic units or a device containing the above fluidic units can include a controller configured to control fluid flow through the above fluidic units, for example, by controlling a pneumatic force applied to a fluidic chamber via a venting port or by controlling pumps an/or valves in fluid communication with microfluidic channels of the fluidic units. For example, the controller can be configured to control the pressure P10 at the venting port of fluidic unit 23011, the pressure P20 at the venting port of fluidic unit 23021, the pressure P30 at the venting port of fluidic unit 23031, the pressure P40 at the venting port of fluidic unit 23041, the pressure P10 at the venting port of fluidic unit 24001, the pressure P20 at the venting port of fluidic unit 24002, the pressure P30 at the venting port of fluidic unit 24003, the pressure P40 at the venting port of fluidic unit 24004, the pressure P50 at the venting port of fluidic unit 24005, the pressure P60 at the venting port of fluidic unit 24006, the pressure P70 at the venting port of fluidic unit 24007, the pressure P80 at the venting port of fluidic unit 24008, the pressure P90 at the venting port of fluidic unit 24009, and/or the pressure P100 at the venting port of fluidic unit 24010. The controller can also be configured to control pumps and/or valves in any of the fluidic conduits, for example, to allow a pressurized, gravity or capillary action flow through the conduits. The pressures can be controlled, for example, in accordance with the equations described above.

Embodiments for Biological Tests: Flow Cytometer Analysis

Figure 25:
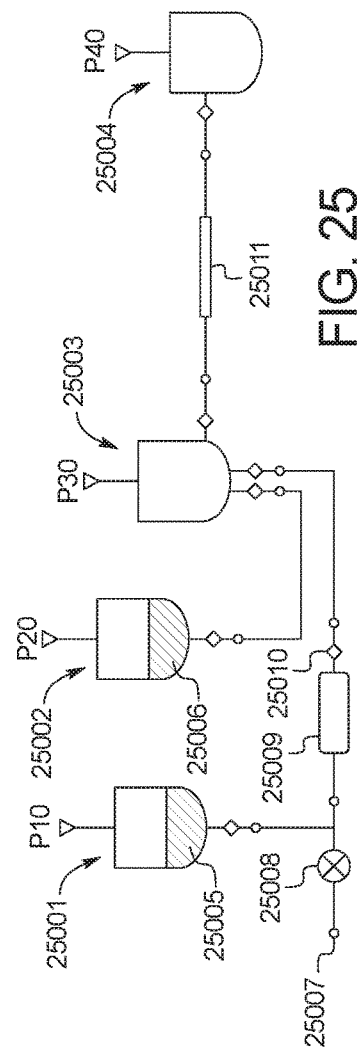
FIG. 25 shows an example embodiment of a fluidic circuit according to the present disclosure.

FIG. 25 shows a cartridge device for flow cytometer analysis. This cartridge has four fluidic units for sample preparation and a sheathless channel 25011 for the cytometer measurement. In Step 1, a biological sample is drawn by capillary force into retaining chamber 25009 and stops at capillary break 25010. In Step 2, valve 25008 is closed to seal off inlet 25007. In Step 3, a first reagent 25005 is transferred out of fluidic unit 25001 and flushes the sample into the unit 25003 for mixing. After being incubated for a certain period of time, the mixture forms a once-diluted sample. In Step 4, a second reagent 25006 is also transferred from fluidic unit 25002 into fluidic unit 25003 for mixing and incubation. After being incubated for a certain period of time, the mixture forms a twice-diluted sample, which then flows through sheathless channel 25011 for sensing such as optical measurements in flow cytometers. The measurement waste is transferred to fluidic unit 25004 for storage. In one embodiment, the biological sample is whole blood, the first reagent is fluorophore-conjugated antibody to label lymphocyte subsets and the second reagent is a lyse solution to break up the undesired RBCs in the sample. This embodiment can be used for cytometer analysis of lymphocyte subsets that is commonly used in immunology and infectious diseases diagnostics. In other embodiments, this cartridge device can be used for other cytometer analyses with different samples and reagents. For example, it can be used for an analysis of bead-based assays, or other cytometer assays known to those skilled in the art.

In an embodiment, a device containing a fluidic cartridge with the above fluidic units or a device containing the above fluidic units can include a controller configured to control fluid flow through the above fluidic units, for example, by controlling a pneumatic force applied to a fluidic chamber via a venting port or by controlling pumps an/or valves in fluid communication with microfluidic channels of the fluidic units. For example, the controller can be configured to control the pressure P10 at the venting port of fluidic unit 25001, the pressure P20 at the venting port of fluidic unit 25002, the pressure P30 at the venting port of fluidic unit 25003, and/or the pressure P40 at the venting port of fluidic unit 25004. The controller can also be configure to control pumps and/or valves in any of the fluidic conduits, for example, to allow a pressurized, gravity or capillary action flow through the conduits. The pressures can be controlled, for example, in accordance with the equations described above.

Figure 26:
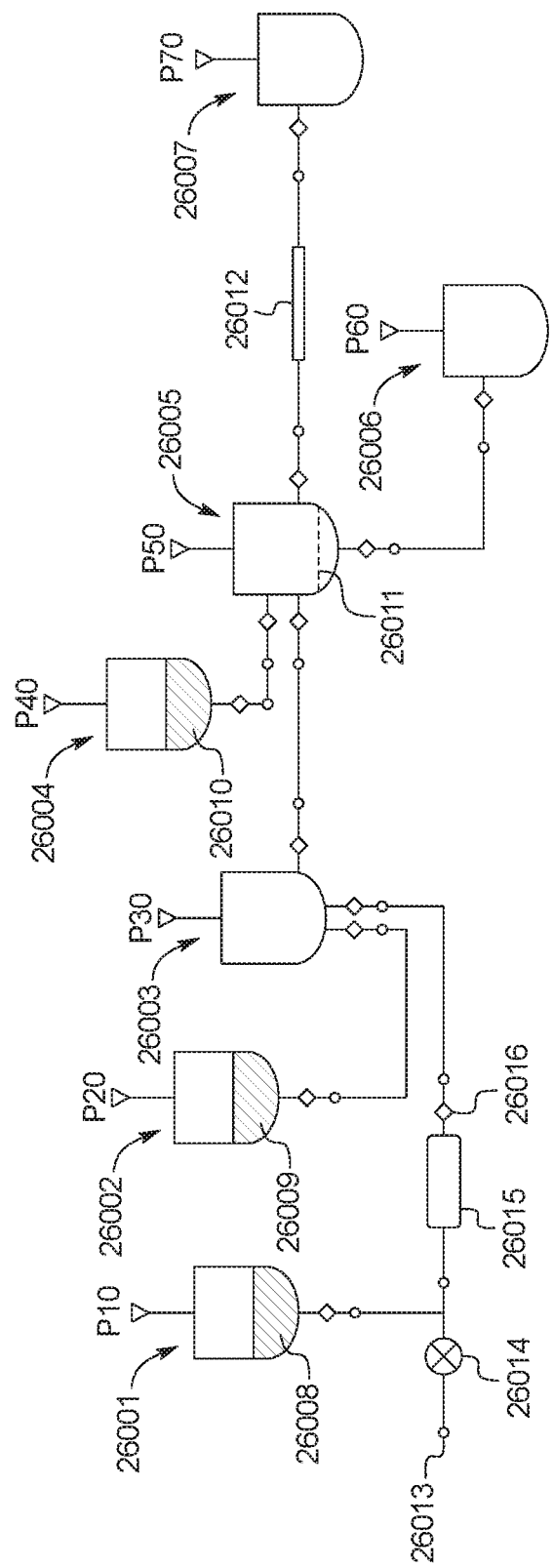
FIG. 26 shows an example embodiment of a fluidic circuit according to the present disclosure.

FIG. 26 shows another example embodiment of a cartridge device for flow cytometer analysis. The first four steps are similar to the cartridge of FIG. 25, collecting a biological sample and forming a twice-diluted mixture in the unit 26003. In Step 5, the mixture is transferred to fluidic unit 26005. It is noted that fluidic unit 26005 has a filter membrane 26011 that has a pore size smaller than the target cells of the sample. In Step 6, excessive fluid in the sample is transferred to a waste reservoir unit 26006 and the target cells are collected above the filter membrane 26011. In Step 7, a third reagent 26010 is transferred into fluidic unit 26005 to re-suspend the target cells in fluid. Steps 6 and 7 together consist of a wash step common in flow cytometer analysis and can be repeated multiple times to purify the target cells from other undesired components of the sample. In Step 8, the fluid suspension of the target cells flows through the sheathless channel 26012 for sensing such as an optical measurement. In an embodiment, the biological sample is whole blood, the first reagent is fluorophore-conjugated antibody to label WBC subsets, the second reagent is a non-isotonic solution to lyse the RBCs and the third reagent is an isotonic dilution buffer. The filter membrane 26011 can have a pore size smaller than the WBCs but larger than the RBCs, wherein target WBCs are labeled with the fluorophore-conjugated antibody and purified from other cellular components such as debris of RBC lysis before the cytometer sensing. In other embodiments, the cartridge device can be used for other cytometer analysis with different samples and reagents. For example, the cartridge device can be used for analysis of bead-based assays, or other cytometer assays known to people skilled in the art. Other cartridge variations can also be used for flow cytometer analysis.

In an embodiment, a device containing a fluidic cartridge with the above fluidic units or a device containing the above fluidic units can include a controller configured to control fluid flow through the above fluidic units, for example, by controlling a pneumatic force applied to a fluidic chamber via a venting port or by controlling pumps an/or valves in fluid communication with microfluidic channels of the fluidic units. For example, the controller can be configured to control the pressure P10 at the venting port of fluidic unit 26001, the pressure P20 at the venting port of fluidic unit 26002, the pressure P30 at the venting port of fluidic unit 26003, the pressure P40 at the venting port of fluidic unit 26004, the pressure P50 at the venting port of fluidic unit 26005, the pressure P60 at the venting port of fluidic unit 26006, and/or the pressure P70 at the venting port of fluidic unit 26007. The controller can also be configure to control pumps and/or valves in any of the fluidic conduits, for example, to allow a pressurized, gravity or capillary action flow through the conduits. The pressures can be controlled, for example, in accordance with the equations described above.

Embodiments for Biological Tests: Clinical Chemistry

Figure 27:
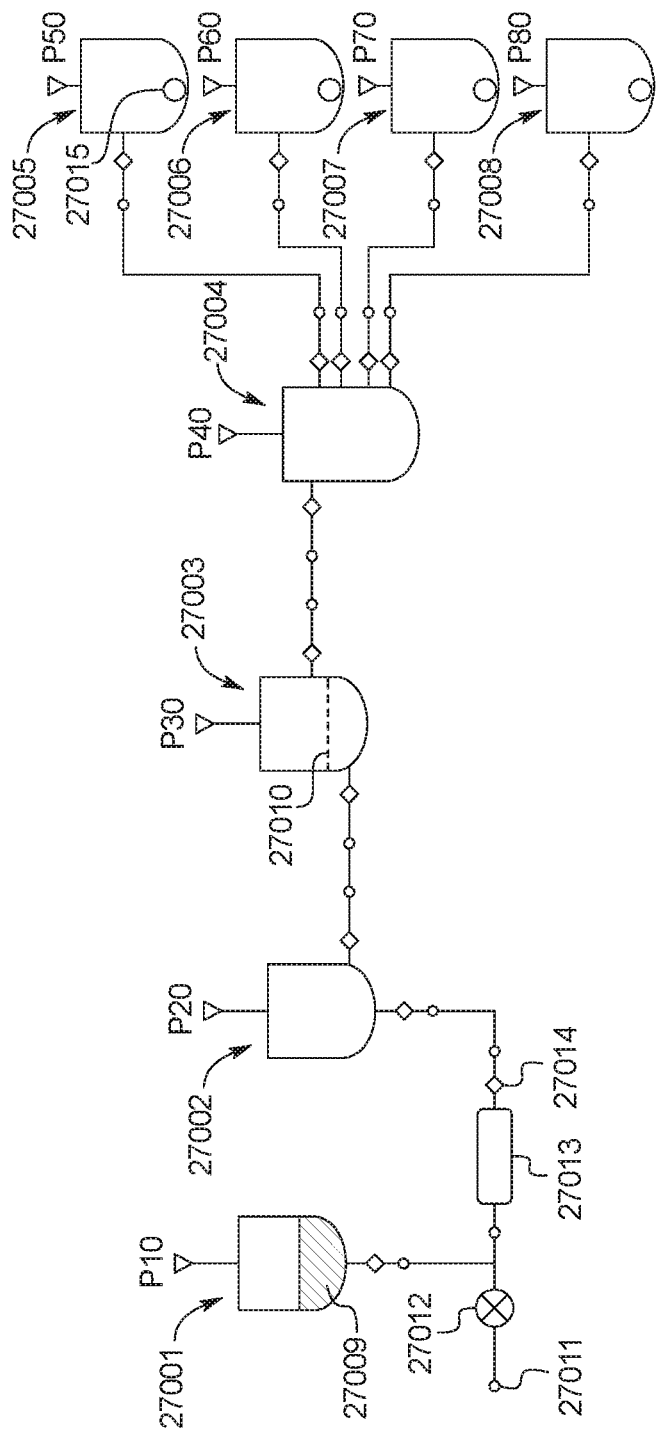
FIG. 27 shows an example embodiment of a fluidic circuit according to the present disclosure.

FIG. 27 shows a cartridge device for clinical chemistry analysis. In Step 1, a biological sample is loaded into the sample-retaining chamber 27013 via the inlet 27011. In Step 2, the valve 27012 is closed to seal off the inlet. In Step 3, a first reagent 27009 is transferred out of the fluidic unit 27001 and flushes the sample into fluidic unit 27002 for mixing. In Step 4, the mixed sample is transferred into fluidic unit 27003 with a filter membrane 27010. This filter stops particles larger than the pore size and allows other fluidic component to pass through. In Step 5, a known volume of the fluid that passes through the filter is transferred into the unit 27004. In step 6, a plurality of known volumes of the fluid is transferred into a plurality of reaction chambers, e.g. fluidic units 27005, 27006, 27007 and 27008, respectively. The known volumes can be determined by the height of the fluid channels with respect to fluidic unit 27004. In the reaction chambers, the fluid mixes and reacts with reagents 27015 initially stored in the chambers respectively for sensing measurement. In an embodiment, the biological sample can be whole blood, plasma or serum. The first reagent can be an isotonic buffer. The filter membrane can have a pore size small enough to remove all cellular components such as WBCs, RBCs and platelets from the sample. The reagents initially stored in the reaction chambers can be dried reagents that dissolve when mixed with the fluid, wherein the serum or plasma component of the sample can be diluted, filtered and transferred to the reaction chambers to react with the reagent beads. Optical measurements such as spectrometer or other measurements can be performed in each chamber to determine concentrations of a target clinical chemistry analyte. With a known volume of the biological sample and a known volume of the isotonic buffer, the initial concentrations of the analyte can be calculated from the measurement data. Furthermore, with a known volume percentage of plasma or serum in a whole blood sample, the initial concentrations of the analyte in terms of plasma or serum can also be obtained.

In an embodiment, a device containing a fluidic cartridge with the above fluidic units or a device containing the above fluidic units can include a controller configured to control fluid flow through the above fluidic units, for example, by controlling a pneumatic force applied to a fluidic chamber via a venting port or by controlling pumps an/or valves in fluid communication with microfluidic channels of the fluidic units. For example, the controller can be configured to control the pressure P10 at the venting port of fluidic unit 27001, the pressure P20 at the venting port of fluidic unit 27002, the pressure P30 at the venting port of fluidic unit 27003, the pressure P40 at the venting port of fluidic unit 27004, the pressure P50 at the venting port of fluidic unit 27005, the pressure P60 at the venting port of fluidic unit 27006, the pressure P70 at the venting port of fluidic unit 27007, and/or the pressure P80 at the venting port of fluidic unit 27008. The controller can also be configure to control pumps and/or valves in any of the fluidic conduits, for example, to allow a pressurized, gravity or capillary action flow through the conduits. The pressures can be controlled, for example, in accordance with the equations described above.

Figure 28:
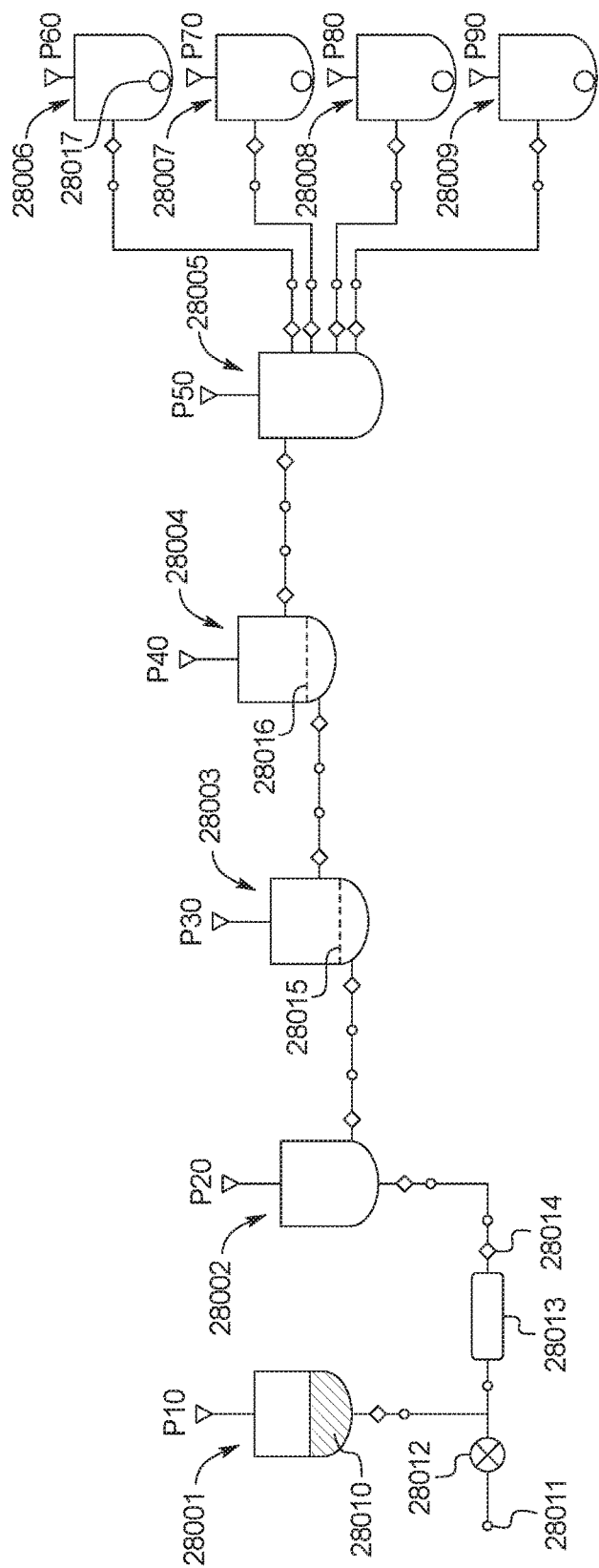
FIG. 28 shows an example embodiment of a fluidic circuit according to the present disclosure.

FIG. 28 shows another embodiment of a cartridge device for the clinical chemistry analysis. In this device, a two-stage filtering can be used to improve the filter efficiency and to minimize RBC hemolysis. The filtering step in FIG. 27 can be replaced with two fluidic units, 28003 and 28004, each of which has a filter membrane 28015 and 28016, respectively. In one embodiment, filter membrane 28015 has a pore size smaller than RBCs but larger than platelets, whereas filter membrane 28016 has a pore size smaller than platelets. In this device, the flow pressure required to drive fluid to pass through membrane 28015 is lower than in the design unit 27003 of FIG. 27, so the RBCs can be removed from the sample with reduced possibility of hemolysis. The flow pressure required to drive fluid to pass through the membrane 28016 is also lower than in the design unit 27003 of FIG. 27, so the possibility of breaking up platelets is also reduced. By avoiding hemolysis, the sensitivity and accuracy of the clinical chemistry analysis can be improved.

In an embodiment, a device containing a fluidic cartridge with the above fluidic units or a device containing the above fluidic units can include a controller configured to control fluid flow through the above fluidic units, for example, by controlling a pneumatic force applied to a fluidic chamber via a venting port or by controlling pumps an/or valves in fluid communication with microfluidic channels of the fluidic units. For example, the pressure P10 at the venting port of fluidic unit 28001, the pressure P20 at the venting port of fluidic unit 28002, the pressure P30 at the venting port of fluidic unit 28003, the pressure P40 at the venting port of fluidic unit 28004, the pressure P50 at the venting port of fluidic unit 28005, the pressure P60 at the venting port of fluidic unit 28006, the pressure P70 at the venting port of fluidic unit 28007, the pressure P80 at the venting port of fluidic unit 28008, and/or the pressure P90 at the venting port of fluidic unit 28009. The controller can also be configure to control pumps and/or valves in any of the fluidic conduits, for example, to allow a pressurized, gravity or capillary action flow through the conduits. The pressures can be controlled, for example, in accordance with the equations described above.

Other variations of cartridge device can also be used for clinical chemistry analysis. In different embodiments, various chemistry parameters such as the basic metabolic panels, the complete metabolic panels, the lipid panels, glucose concentration, C-Reactive Protein concentration, HbA1C hemoglobin concentration, D-dimer, Creatinine, Albumin etc. can be measured as well. Various samples such as whole blood, plasma, serum, urine, etc. can also be measured.

Embodiments for Biological Tests: Immunoassay

Figure 29:
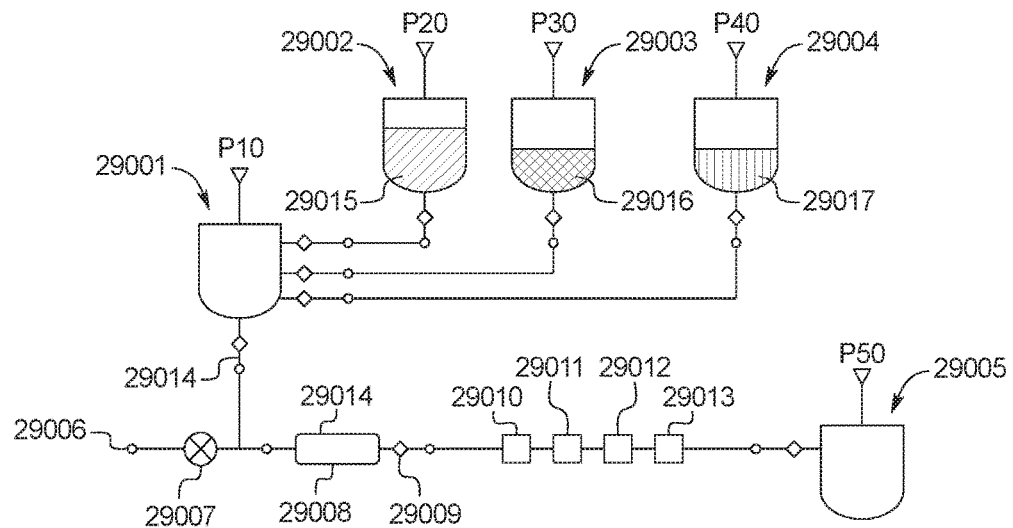
FIG. 29 shows an example embodiment of a fluidic circuit according to the present disclosure.

FIG. 29 shows a cartridge device for immunoassay tests such as an ELISA assay. In this cartridge, fluidic unit 29001 is a flow relay to transfer sample and reagents in sequential to sensing zones. In Step 1, a biological sample 29014 is loaded into a volumetric chamber 29008 via a sample inlet 29006. In Step 2, valve 29007 is closed to seal off the inlet port. In Step 3, air is pumped out of the unit 29001 and pushes the sample 29014 to flow over the sensing zones 29010, 29011, 29012 and 29013. In Step 4, a first reagent 29015, a second reagent 29016 and a third reagent 29017 are transferred in serial into and then out of the unit 29001, so as to flow over the sensing zones in sequential. The sample and reagents enters the waste reservoir unit 29005 after flowing over the sensing zones. In one embodiment, the biological sample can be whole blood, plasma or serum. The sensing zones can be initially coated with a primary antigen and a blocking reagent. The blocking reagent, e.g. a neutral protein such as BSA, blocks sites on the sensing zones that are not occupied by the primary antigen. When the sample flows over, the coated antigen captures the target antibodies onto the sensing zones. The first reagent can be a wash buffer to remove residual sample, and the second reagent can be an enzyme-conjugated secondary antibody that further binds to the target antibodies captured. The third reagent can be a substrate to react with the enzyme for colorimetric measurement. The sensing zones can be washed with the first reagent multiple times if needed. In other embodiments, the second reagent can be a fluorophore-conjugated secondary antibody that allows fluorescent measurement without the colorimetric reaction of the third reagent. In yet other embodiments, the cartridge device can be used with other combination of reagents for different ELISA assays, such as a direct, an indirect sandwich assay, etc., which are known to person skilled in the art.

In an embodiment, a device containing a fluidic cartridge with the above fluidic units or a device containing the above fluidic units can include a controller configured to control fluid flow through the above fluidic units, for example, by controlling a pneumatic force applied to a fluidic chamber via a venting port or by controlling pumps an/or valves in fluid communication with microfluidic channels of the fluidic units. For example, the controller can be configured to control the pressure P10 at the venting port of fluidic unit 29001, the pressure P20 at the venting port of fluidic unit 29002, the pressure P30 at the venting port of fluidic unit 29003, the pressure P40 at the venting port of fluidic unit 29004, and/or the pressure P50 at the venting port of fluidic unit 29005. The controller can also be configure to control pumps and/or valves in any of the fluidic conduits, for example, to allow a pressurized, gravity or capillary action flow through the conduits. The pressures can be controlled, for example, in accordance with the equations described above. The controller can also be configured to control the sensing and analysis that occurs at zones 29010, 29011, 29012 and 29013.

Figure 30:
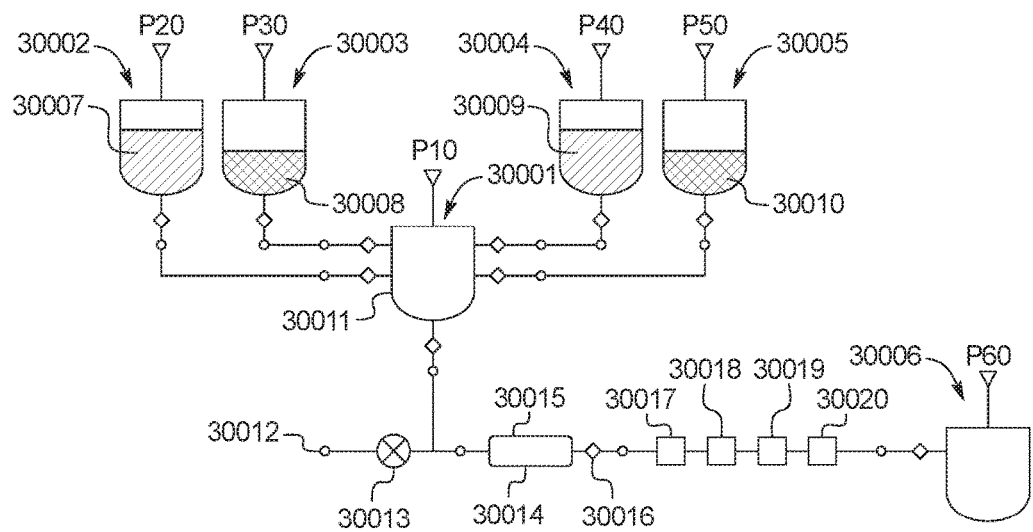
FIG. 30 shows an example embodiment of a fluidic circuit according to the present disclosure.

FIG. 30 is another embodiment of a cartridge device for immunoassays such as an ELISA assay. In comparison to FIG. 29, more units are used to store reagents. In addition, two or more of the stored reagents can be transferred into fluidic unit 30001 for mixing and reaction, before being further transferred to flow over the sensing zones. In one embodiment, the reagents 30007, 30008, 30009 and/or 30010 can be mixed in the unit 30001 for chemical or biological reactions to forms a freshly prepared reagent, which can flow over the sensing zones within a predetermined time period. In an embodiment, this cartridge device can be used to perform an immunoassay for human IgG in blood, which uses silver enhancement for signal amplification. The reagents 30007, 30009 can be a solution of silver salts and the reagents 30008, 30010 can be a solution of hydroquinone. These two reagents produce signal amplification upon mixing and are stored in separated units before test. In addition of the devices of FIG. 29 and FIG. 30, other variations of cartridges can also be designed to perform different immunoassays.

In an embodiment, a device containing a fluidic cartridge with the above fluidic units or a device containing the above fluidic units can include a controller configured to control fluid flow through the above fluidic units, for example, by controlling a pneumatic force applied to a fluidic chamber via a venting port or by controlling pumps an/or valves in fluid communication with microfluidic channels of the fluidic units. For example, the controller can be configured to control the pressure P10 at the venting port of fluidic unit 30001, the pressure P20 at the venting port of fluidic unit 30002, the pressure P30 at the venting port of fluidic unit 30003, the pressure P40 at the venting port of fluidic unit 30004, the pressure P50 at the venting port of fluidic unit 30005, and/or the pressure P60 at the venting port of fluidic unit 30006. The controller can also be configure to control pumps and/or valves in any of the fluidic conduits, for example, to allow a pressurized, gravity or capillary action flow through the conduits. The pressures can be controlled, for example, in accordance with the equations described above. The controller can also be configured to control the sensing and analysis that occurs at zones 30017, 30018, 30019, 30020.

Embodiments for Biological Tests: Molecular Diagnostics

Figure 31:
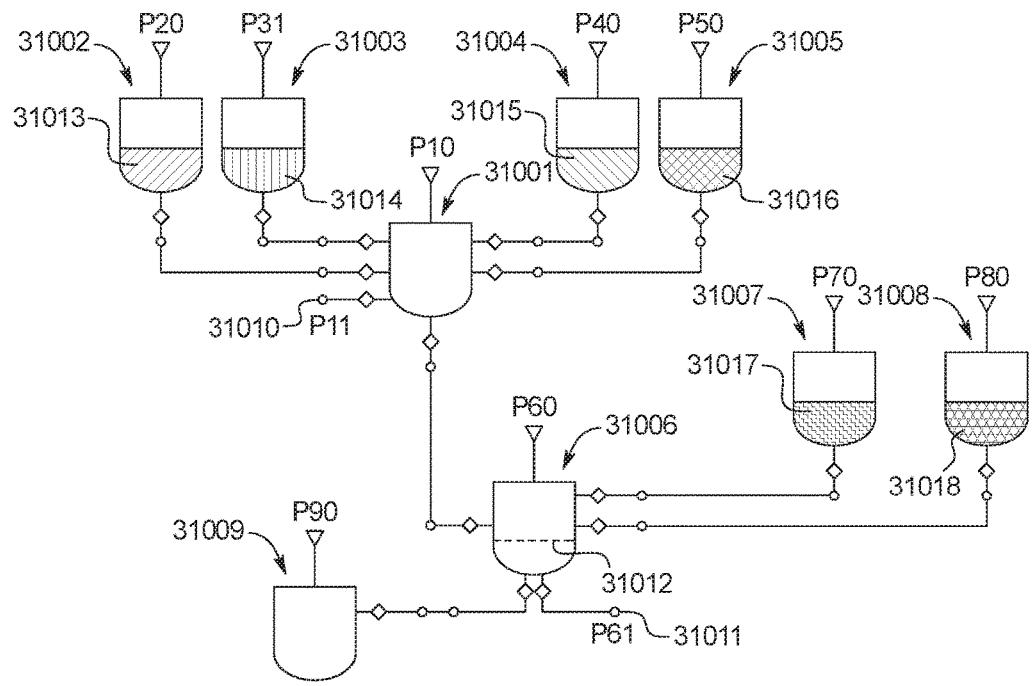
FIG. 31 shows an example embodiment of a fluidic circuit according to the present disclosure.

Embodiments of this fluidic unit can also be used for molecule diagnostics. FIG. 31 shows an embodiment of a cartridge device to purify nucleic acid from a biological sample. In Step 1, a biological sample with cells for nucleic acid purification is transferred into fluidic unit 31001 via inlet channel 31010. In Step 2, a first reagent 31013, a second reagent 31014, a third reagent 31015 and a fourth reagent 31016 can be transferred into the unit 31001 in serial for mixing and incubation. In an embodiment, the first reagent 31013 can be a proteinase K solution, which breaks down cell membranes and releases cellular mass and the nucleic acids into the fluid. The second reagent 31014 can be a detergent solution that lyses cells and solubilizes the cellular mass excluding the nucleic acids, the third reagent 31015 can be a binding solution that increases the affinity of the nucleic acids binding to a silica surface, and the fourth reagent 31016 can be fluid suspension of beads that has a silica surface coating. Upon incubation, the beads can capture the released nucleic acids in the fluid at the end of the Step 2. In Step 3, the sample mixture can be transferred into fluidic unit 31006 with a filter membrane 31012. In an embodiment, the pore size of this filter membrane 31012 can be smaller than the beads, and thus trap the beads above the membrane and allow excess fluid to pass through. In Step 4, the excess fluid can then be transferred into waste reservoir unit 31009. In Step 5, a fifth reagent 31017 from fluidic unit 31007 can be transferred into fluidic unit 31006. In an embodiment, the fifth reagent 31017 can be a wash buffer to purify the captured beads. Excess fluid can then be transferred into the waste reservoir unit 31009 and the wash step can be repeated multiple times if needed. In Step 6, a sixth reagent 30108 from fluidic unit 31008 can be transferred into fluidic unit 31006. In an embodiment, the sixth reagent 30108 can be an elution buffer, which releases the nucleic acids from the beads binding. Finally, the elusion buffer containing the released nucleic acids can be transferred out of channel 31011 for further analysis, whereas the beads are trapped above the filter membrane. Other embodiments of this cartridge can also involve different reagents, thermal treatment to accelerate or stabilize the reactions, and other variations to optimize the nucleic acid purification process.

In an embodiment, a device containing a fluidic cartridge with the above fluidic units or a device containing the above fluidic units can include a controller configured to control fluid flow through the above fluidic units, for example, by controlling a pneumatic force applied to a fluidic chamber via a venting port or by controlling pumps an/or valves in fluid communication with microfluidic channels of the fluidic units. For example, the pressure P10 at the venting port of fluidic unit 31001, the pressure P20 at the venting port of fluidic unit 31002, the pressure P30 at the venting port of fluidic unit 31003, the pressure P40 at the venting port of fluidic unit 31004, the pressure P50 at the venting port of fluidic unit 31005, the pressure P60 at the venting port of fluidic unit 31006, the pressure P70 at the venting port of fluidic unit 31007, the pressure P80 at the venting port of fluidic unit 31008, and/or the pressure P90 at the venting port of fluidic unit 31009. The controller can also be configure to control pumps and/or valves in any of the fluidic conduits, for example, to allow a pressurized, gravity or capillary action flow through the conduits. The pressures can be controlled, for example, in accordance with the equations described above.

Figure 32:
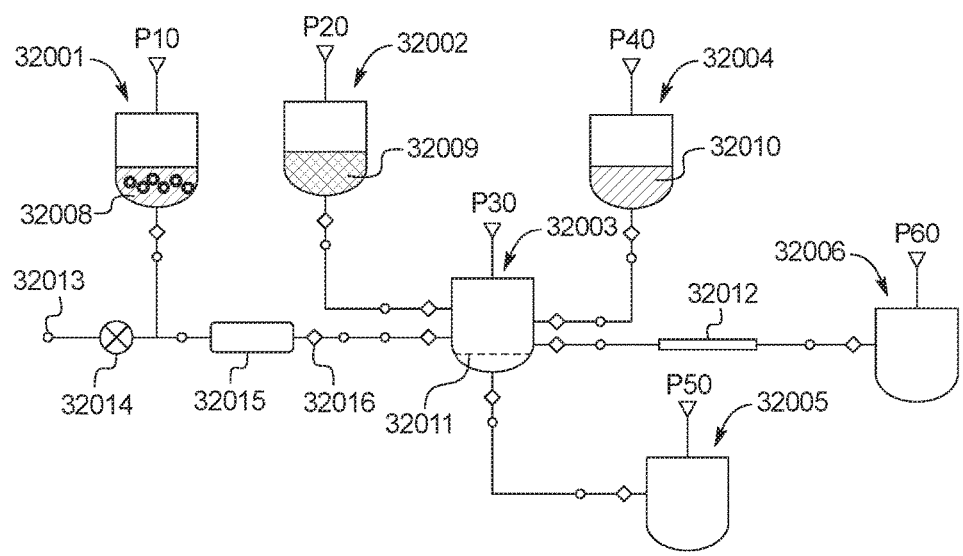
FIG. 32 shows an example embodiment of a fluidic circuit according to the present disclosure.

Other variations of cartridge devices can further include PCR steps to amplify the purified nucleic acids and/or measurement steps to determine the quantity of the nuclide acids. FIG. 32 shows a cartridge device for bead-based flow cytometer analysis to determine the quantity of nucleic acids. In Step 1, a sample containing DNA segments is drawn into a retaining chamber 32015. In Step 2, valve 32014 is closed to seal off the inlet 33005. In Step 3, a first reagent 32008 from fluidic unit 32001 can be transferred out of fluidic unit 32001 and flush the sample into fluidic unit 32003 for mixing and incubation. In an embodiment, the first reagent 32008 can be a fluid suspension of beads that are initially coated with probes to capture DNA segments. The beads can be coated with multiple types of probes for analysis of multiple types of DNA segments. In Step 4, a second reagent 32009 from fluidic unit 32002 can be transferred into fluidic unit 32003 for mixing and incubation with the sample. In an embodiment, the second reagent 32009 can be a fluorophore-conjugated probe to bind to the captured DNA segments. Upon incubation, the DNA segments captured on the beads are further labeled with fluorophore. In Step 5, excess fluid can be transferred out of fluidic unit 32003 and into a waste reservoir unit 32005, whereas the beads are trapped above filter membrane 32011. Next, a third reagent 32010 can be transferred from fluidic unit 32004 into fluidic unit 32003 to re-suspend the beads. In one embodiment, the third reagent 32010 can be a wash buffer and Step 5 washes away excessive fluorophore to reduce the background noise. This wash step can be repeated multiple times if needed. In Step 6, the prepared sample is transferred into sheathless channel 32012 for cytometer analysis such as fluorescence detection to determine the quantity of the DNA segments. The measurement waste is transferred into waste reservoir unit 32006.

In an embodiment, a device containing a fluidic cartridge with the above fluidic units or a device containing the above fluidic units can include a controller configured to control fluid flow through the above fluidic units, for example, by controlling a pneumatic force applied to a fluidic chamber via a venting port or by controlling pumps an/or valves in fluid communication with microfluidic channels of the fluidic units. For example, the controller can be configured to control the pressure P10 at the venting port of fluidic unit 32001, the pressure P20 at the venting port of fluidic unit 32002, the pressure P30 at the venting port of fluidic unit 32003, the pressure P40 at the venting port of fluidic unit 32004, the pressure P50 at the venting port of fluidic unit 32005, and/or the pressure P60 at the venting port of fluidic unit 32006. The controller can also be configure to control pumps and/or valves in any of the fluidic conduits, for example, to allow a pressurized, gravity or capillary action flow through the conduits. The pressures can be controlled, for example, in accordance with the equations described above. The controller can also be configured to control the sensing and analysis that occurs at sheathless channel 32012.

Embodiments for Biological Tests: Blood Gas

Figure 33:
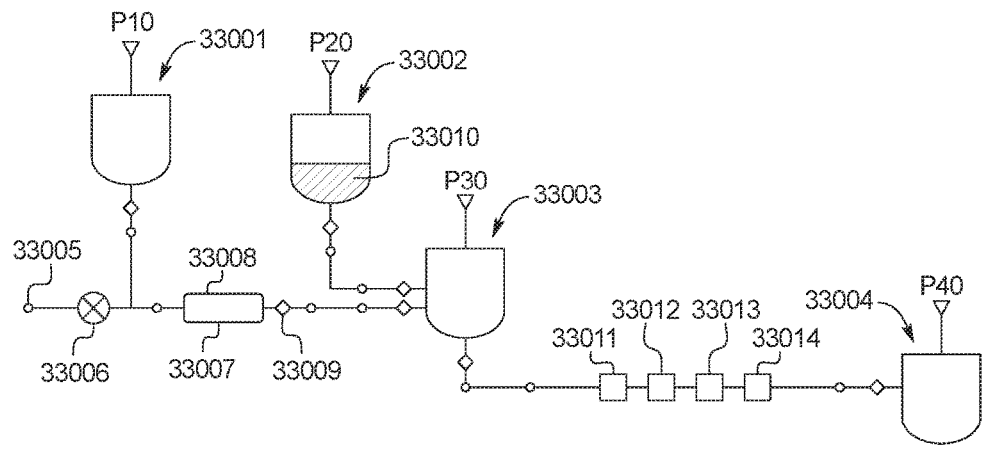
FIG. 33 shows an example embodiment of a fluidic circuit according to the present disclosure.

FIG. 33 shows a cartridge device for blood gas analysis. In Step 1, a biological sample 33008 such as whole blood or plasma or serum is draw into the retaining chamber 33007 by capillary force and stops at the capillary break 33009. In Step 2, valve 33006 is closed to seal off inlet 33005, and in Step 3, a first reagent 33010 is relayed from fluidic unit 33002 to fluidic unit 33003 and into the sensing zones 33011, 33012, 33013 for measurement. In an embodiment, first reagent 33010 is a calibration solution. In Step 4, air or a second reagent is transferred out of the unit 33001 and pushes the blood sample 33008 to the chamber for the fluid unit 33003. The blood sample or the mixture of the blood and the second reagent is then further transferred to the sensing zones for measurement. The measurement wastes are collected in reservoir unit 33004. In one embodiment, the sensing zones are fluidic chambers with exposed electrodes, which can be initially coated with reagents for electrochemical sensing of blood gas components. In other embodiments, the electrode can be a layer of metal or a pre-manufactured sensor piece.

In an embodiment, a device containing a fluidic cartridge with the above fluidic units or a device containing the above fluidic units can include a controller configured to control fluid flow through the above fluidic units, for example, by controlling a pneumatic force applied to a fluidic chamber via a venting port or by controlling pumps an/or valves in fluid communication with microfluidic channels of the fluidic units. For example, the controller can be configured to control the pressure P10 at the venting port of fluidic unit 33001, the pressure P20 at the venting port of fluidic unit 33002, the pressure P30 at the venting port of fluidic unit 33003, and/or the pressure P40 at the venting port of fluidic unit 33004. The controller can also be configure to control pumps and/or valves in any of the fluidic conduits, for example, to allow a pressurized, gravity or capillary action flow through the conduits. The pressures can be controlled, for example, in accordance with the equations described above. The controller can also be configured to control the sensing and analysis that occurs at zones 33011, 33012, 33013, 33014.

In addition to the abovementioned embodiments, the cartridges can be used to measure one or multiple of the above biological tests in one cartridge, and/or to perform other biological tests.

Methodology to Compensate Tilting

Figure 34A:
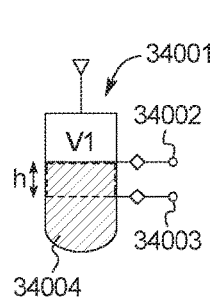
FIGS. 34A to 34G show how embodiments of the present disclosure account for tilting of a fluidic cartridge.
Figure 34B:
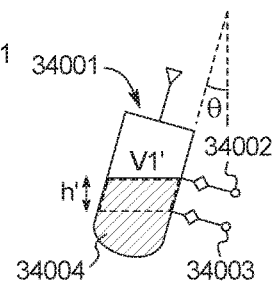

For embodiments of fluidic units and cartridges that utilize gravity, it is desirable to maintain a vertical position. For example, the accuracy of transferring a fixed volume of fluid is sensitive to tilting away from the vertical position, as illustrated in FIG. 34A. Fluidic unit 34001 is designed to transfer a fixed volume V1 with the "self-stop" mechanism, for which the height difference between the two channels 34002 and 34003 is h. When the unit is in a tilted position, as shown in FIG. 34B, the height difference between the two channel decreases to h'=h cos θ. The volume transferred V1' differs form the designed volume with a deviation of ΔV=V1'−V1, which is dependent on the tile angle θ and the geometry of the chamber. Three methodologies are taught in the present disclosure to compensate this deviation.

Figures 34C, 34D:
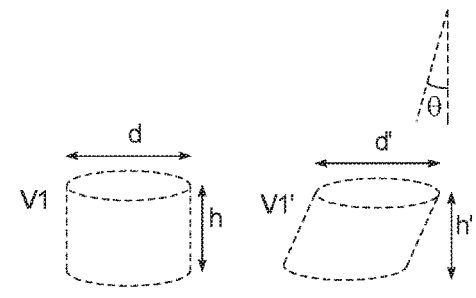

The first methodology is to design a chamber with a desirable geometry to compensate the deviation. For example, the chamber of unit 34001 can be a cylinder, as shown in FIG. 34C, wherein the diameter d of the fluid stored in the cylinder becomes d'=d/cos θ after tilting, as shown in FIG. 34D. Therefore, the volume deviation can be calculated as follow:

$$\Delta V=V1'-V1=V1\div\cos\theta-V1=(1/\cos\theta-1)V1 \qquad [10]$$

Figure 34E:
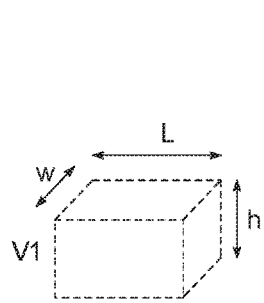
Figure 34F:
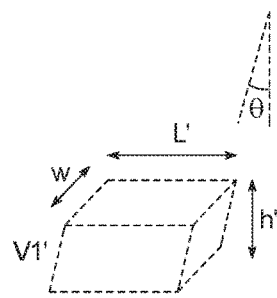

For another example, the chamber of unit 34001 is a rectangular cuboid as shown in FIG. 34E. When the tilting is only in the direction of the edge L, as shown in FIG. 34F, the length of the cuboid becomes L'=L/cos θ and the width remains w'=w (no tilt in the direction of the edge w). Therefore, the volume deviation can be calculated as following:

$$\Delta V=V1'-V1=h\cos\theta\times L/\cos\theta\times w-hLw=0 \qquad [11]$$

The rectangular cuboid geometry is more preferable to the cylinder geometry to compensate the volume deviation, when the tilt is at certain angle. Other variations of the chamber geometry, such as a circular cone frustum, can be used to compensate the volume deviation, when the tilt can be at any angle.

The second methodology is to measure the tilt angle θ with a tilt sensor, such as a tiltmeter or an inclinometer, wherein the volume deviation can be calculated, as shown in the examples of Equation [10] and Equation [11]. The calculated volume deviation can be used as a parameter to compensate tilt for the biological test data measured on the cartridge. Furthermore, tilting of the cartridge can be monitored before, during and after the biological tests continuously. Therefore, not only tilting but also vibration, which can be interpreted as continuous changing of tilt angle, can be monitored and compensated as well. Various tiltmeters or inclinometers can be used for this purpose, either embodied on the cartridge or installed separately in a reader instrument that receives the cartridge. In one embodiment, the tiltmeter can be a MEMS accelerator-based tiltmeter, which has the merits of low cost, high reliability, large measurement range, and a resolution of 0.1 to 1 degree.

Figure 34G:
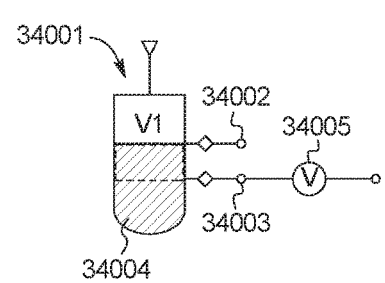

The third methodology is to add a flow sensor 34005 at the outlet of the unit, as shown in the example of FIG. 34G. The flow sensor can measure the precise volume V1' being transferred and is independent on the tilting. Various flow sensors can be used for this purpose.

Reader Devices to Work with Cartridges

The cartridges of the present disclosure are inserted into a reader instrument for signal readout. The reader instrument can be designed to accept one cartridge at a time, or multiple cartridges at a time. By running multiple cartridges in serial, in parallel, or in a streamline configuration, a high test-throughput can be achieved. The streamline configuration means that multiple cartridges are run in parallel for the sample preparation stage and run in serial for the signal sensing stage. In this streamline configuration, only one set of external sensing components is needed for the signal readout. In other embodiments, the reader instrument can be designed to accommodate only one type of cartridge, such as cartridge for measuring Complete Blood Count, or to accommodate multiple types of cartridges, such as cartridges for Complete Blood Count, Blood Chemistry, Immunoassay, etc. In other embodiments, the reader instrument is designed to read cartridge that integrates multiple types of biological tests.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the disclosure and does not pose a limitation on the scope of the disclosure otherwise claimed. No language in the specification should be construed as indicating any non-claimed element essential to the practice of the disclosure.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of the disclosure are described herein, including the best mode known to the inventors for carrying out the disclosure. Of course, variations on those preferred embodiments will become apparent to those of ordinary skill in the art upon reading the foregoing description. The inventor expects those of ordinary skill in the art to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

Further, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The invention is claimed as follows:

1. A fluidic device for analyzing a fluid sample, the fluidic device comprising:
   a cartridge device configured to receive the fluid sample, the cartridge device including:
   a fluidic chamber;
   at least one microfluidic channel in fluid communication with the fluidic chamber;
   a venting port configured to apply a pneumatic force to the fluidic chamber; and
   at least one passive valve located within the at least one microfluidic channel and configured to allow or stop fluid flow through the at least one microfluidic channel based on a pressure difference; and
   a controller configured to control the pneumatic force applied to the fluidic chamber via the venting port,
   wherein the cartridge device is configured to be received by the fluidic device in a vertical or tilted position such that at least a portion of fluid inside the fluidic chamber is pulled by gravity in a direction away from the venting port or towards a bottom of the fluidic chamber.

2. The fluidic device of claim 1, wherein the cartridge device is configured to be held in the vertical position by a housing of the fluidic device.

3. The fluidic device of claim 2, wherein the venting port is located at a top portion of the fluidic chamber when the fluidic chamber is held in the vertical position.

4. The fluidic device of claim 2, wherein the at least one microfluidic channel is located a height below the venting port when the fluidic chamber is held in the vertical position.

5. The fluidic device of claim 2, wherein the at least one microfluidic channel includes a first microfluidic channel and a second microfluidic channel, the first microfluidic channel located a height above the second microfluidic channel with the fluidic chamber held in the vertical position.

6. The fluidic device of claim 1, wherein the at least one passive valve includes at least one of: (i) a hydrophobic patch; (ii) a hydrophilic patch; (iii) a sudden diameter enlargement of a hydrophobic channel; and (iv) a sudden diameter shrink of a hydrophobic channel.

7. The fluidic device of claim 1, wherein the controller is configured to control the pneumatic force applied to the fluidic chamber via the venting port based on (i) a pressure ($P_0$) associated with the venting port, and (ii) a pressure ($P_1$) associated with the at least one microfluidic channel.

8. The fluidic device of claim 7, wherein the controller is configured to store fluid in the fluidic chamber by controlling the pneumatic force applied to the fluidic chamber via the venting port according to the following equations:

$$-\Delta P_{in}-\rho gh \leq P_0-P_1 \leq \Delta P_{out}-\rho gh, \text{ if } h \geq 0; \text{ and}$$

$$P_1-P_0 \leq \Delta P_{in}, \text{ if } h<0,$$

wherein (i) $\Delta P_{in}$ is a first threshold pressure associated with a first direction of fluid entering the fluidic chamber, (ii) $\Delta P_{out}$ is a second threshold pressure associated with a second direction of fluid leaving the fluidic chamber, and (iii) $\rho gh$ is the hydraulic pressure of the fluid.

9. The fluidic device of claim 7, wherein the controller is configured to transfer fluid into the fluidic chamber by controlling the pneumatic force applied to the fluidic chamber via the venting port according to the following equations:

$$P_1-P_0 > \Delta P_{in}+\rho gh, \text{ if } h \geq 0; \text{ and}$$

$$P_1-P_0 > \Delta P_{in}, \text{ if } h<0,$$

wherein (i) $\Delta P_{in}$ is a threshold pressure associated with a direction of fluid entering the fluidic chamber, and (ii) $\rho gh$ is the hydraulic pressure of the fluid.

10. The fluidic device of claim 7, wherein the controller is configured to transfer fluid out of the fluidic chamber by controlling the pneumatic force applied to the fluidic chamber via the venting port according to the following equation:

$$P_0-P_1 > \Delta P_{out}-\rho gh,$$

wherein (i) $\Delta P_{out}$ is a threshold pressure associated with a direction of fluid leaving the fluidic chamber, and (ii) $\rho gh$ is the hydraulic pressure of the fluid.

11. The fluidic device of claim 1, wherein the fluidic chamber includes at least one filter membrane with a pore size smaller than known particles in the fluid.

12. The fluidic device of claim 1, wherein the cartridge device includes a plurality of fluidic chambers, and wherein the controller controls the pneumatic pressure applied to respective venting ports of the plurality of fluidic chambers independently of each other.

13. The fluidic device of claim 12, wherein the plurality of fluidic chambers includes a first fluidic chamber and a second fluidic chamber, the first fluidic chamber and the second fluidic chamber in fluid communication via only one microchannel.

14. The fluidic device of claim 1, wherein the fluidic chamber has a size of about 0.1 mm to 50 mm in width, 0.1 mm to 50 mm in depth and 0.1 mm to 100 mm in height, and wherein the microfluidic channel has a cross section size about 0.1 μm to 5 mm in width and 0.1 μm to 5 mm in depth.

15. The device of claim 1, wherein the cartridge device includes at least two microfluidic channels in fluid communication with the fluidic chamber, and wherein the controller is configured to transfer fluid out of the chamber via at least one of the microfluidic channels.

16. The fluidic device of claim 1, wherein the pneumatic force applied at the venting port is ambient pressure or atmospheric pressure.

17. The fluidic device of claim 1, wherein the fluidic chamber has a volume larger than a volume of the fluid sample received therein, and wherein an air gap exists between the venting port and the fluid sample received therein.

18. The fluidic device of claim 1, wherein the cartridge device is configured to receive a fluid sample with air bubbles in the fluidic chamber, and wherein at least a portion of the air bubbles is separated from the sample in the fluidic chamber by gravity.

19. The fluidic device of claim 18, wherein the controller is configured to generate at least a portion of the air bubbles in the fluid sample by applying a pneumatic force to the cartridge device.

20. The fluidic device of claim 18, wherein the cartridge device is configured to allow at least a portion of the air bubbles to exit the venting port.

21. The fluidic device of claim 1, wherein the controller is configured to transfer the fluid sample out of the fluidic chamber by transferring at least a portion of the fluid sample through one microfluidic channel and at least another portion of the fluid sample through another microfluidic channel.

22. The fluidic device of claim 1, wherein the controller is configured to transfer two or more fluid samples separately into the fluidic chamber to form a sample mixture.

23. The fluidic device of claim 1, wherein the controller is configured to transfer two or more fluid samples separately into the fluidic chamber, and to transfer the two or more fluid samples separately out of the fluidic chamber by flowing the two or more fluid samples through a microfluidic channel.

24. The fluidic device of claim 11, wherein the fluidic chamber is configured to receive a fluid sample with cells, a fluid sample with blood cells, or a fluid sample with particles carrying nucleic acids, and wherein the filter membrane has pore sizes smaller than at least a portion of the cells, the blood cells or the particles carrying nucleic acids.

25. The fluidic device of claim 11, wherein the cartridge device is configured to be in fluid communication with a microfluidic channel on one side of the filter membrane, and to be in fluid communication with another microfluidic channel on another side of the filter membrane.

26. The fluidic device of claim 1, wherein the cartridge device further comprises at least one fluidic structure for sample measurements, and wherein at least one sensing signal is measured from a fluid sample in the fluidic structure.

27. The fluidic device of claim 26, wherein the fluidic structure comprises a sheathless channel for a cytometer analysis of cells or particles in the fluid sample, and wherein at least one of the following signals is measured: (i) an optical sensing signal; and (ii) an impedance sensing signal.

28. The fluidic device of claim 26, wherein the fluidic structure comprises a chamber, and wherein at least one optical sensing signal is measured from a fluid sample in the chamber.

29. The fluidic device of claim 26, wherein the fluidic structure comprises one or more sensing zones, and wherein at least one of the sensing zones is coated with antigens to capture antibodies in a fluid sample in the sensing zones.

30. The fluidic device of claim 26, wherein the fluidic structure comprises one or more electrodes, and wherein at least one electrical signal is measured from a fluid sample in contact with the one or more of electrodes.

* * * * *